US012605404B2

(12) United States Patent
Rude et al.

(10) Patent No.: US 12,605,404 B2
(45) Date of Patent: Apr. 21, 2026

(54) SYNTHETIC CELLULAR MEMBRANE CHEMICAL IONOPHORE DELIVERY SYSTEM COMPRISING HEXA-AQUA LIGAND COMPOSITIONS

(71) Applicant: Ionic Alliance Holdings, LLC, Indian Hills, CO (US)

(72) Inventors: Kevin Walton Rude, Lowell, MI (US); Michael Kenneth Krysiak, Conifer, CO (US); Jasen Eric Petersen, Indian Hills, CO (US)

(73) Assignee: Ionic Alliance Foundation, Inc, Indian Hills, CO (US)

( * ) Notice: Subject to any disclaimer, the term of this patent is extended or adjusted under 35 U.S.C. 154(b) by 277 days.

(21) Appl. No.: 17/390,743

(22) Filed: Jul. 30, 2021

(65) Prior Publication Data

US 2022/0226371 A1 Jul. 21, 2022

Related U.S. Application Data

(63) Continuation-in-part of application No. 17/349,880, filed on Jun. 16, 2021, now abandoned.

(60) Provisional application No. 63/137,088, filed on Jan. 13, 2021.

(51) Int. Cl.

| | |
|---|---|
| ***A61K 33/30*** | (2006.01) |
| ***A61K 9/08*** | (2006.01) |
| ***A61K 33/34*** | (2006.01) |
| ***A61K 33/42*** | (2006.01) |

(52) U.S. Cl.
CPC ................ *A61K 33/30* (2013.01); *A61K 9/08* (2013.01); *A61K 33/34* (2013.01); *A61K 33/42* (2013.01)

(58) Field of Classification Search
CPC .......... A61K 9/08; A61K 33/02; A61K 33/04; A61K 33/30; A61K 33/34
See application file for complete search history.

(56) References Cited

U.S. PATENT DOCUMENTS

| | | | | |
|---|---|---|---|---|
| 871,392 | A | 11/1907 | Ellis | |
| 991,261 | A | 5/1911 | Arlt | |
| 1,620,490 | A | 3/1927 | Sanders | |
| 1,679,919 | A | 8/1928 | Rogers et al. | |
| 1,785,472 | A | 12/1930 | Adler et al. | |
| 2,208,253 | A | 7/1940 | Flenner et al. | |
| 2,269,891 | A | 1/1942 | Verne et al. | |
| 2,456,727 | A | 12/1948 | Nikitin | |
| 2,494,941 | A | 1/1950 | Milton | |
| 2,655,460 | A | 10/1953 | Kise | |
| 2,878,155 | A | 3/1959 | Cruickshank | |
| 2,900,303 | A | 8/1959 | Ernest | |
| 2,901,393 | A | 8/1959 | Magner | |
| 2,938,828 | A | 5/1960 | Der et al. | |
| 3,076,834 | A | 2/1963 | Norton | |
| 3,099,521 | A | 7/1963 | Arensberg | |
| 3,206,396 | A | 9/1965 | Davis | |
| 3,240,701 | A | 3/1966 | Furia | |
| 3,262,846 | A | 7/1966 | Ercegovich | |
| 3,266,913 | A | 8/1966 | Hardy et al. | |
| 3,681,492 | A | 8/1972 | Kotzbauer | |
| 3,782,471 | A | 1/1974 | Felmann et al. | |
| 4,098,602 | A | 7/1978 | Seymour et al. | |
| 4,952,398 | A | 8/1990 | Tapin | |
| 5,830,865 | A * | 11/1998 | Stjernfelt | A61P 7/02 530/331 |
| 7,163,709 | B2 | 1/2007 | Cook et al. | |
| 9,266,785 | B2 | 2/2016 | Kennedy | |
| 2013/0004452 | A1* | 1/2013 | Mehta | A61K 31/122 426/74 |
| 2021/0338721 | A1* | 11/2021 | Simpson | A61K 45/06 |
| 2022/0072037 | A1* | 3/2022 | Kennedy | A61K 33/06 |

OTHER PUBLICATIONS

"Complex Ions", https://www.chem.fsu.edu/chemlab/chm1046course/complexions.html, updated Aug. 15, 2020.
Morais, Jennifer Beatriz Silva, "Role of Magnesium in Oxidative Stress in Individuals with Obesity", Biological Trace Element Research, 176, Jul. 22, 2016, pp. 20-26.
Wikipedia, "Metal Aquo Complex", last edited Feb. 2, 2021.

* cited by examiner

*Primary Examiner* — Michael B. Pallay

(57) ABSTRACT

Synthetic ionophores for the active carry and transport of free ions across biological membranes in vivo, comprising coordination complexes of molecules with polarized hexa-aqua and/or tetra-aqua systems of free ionic metals and ionic salts as the ionophores, useful in transporting pharmaceutical, nutrient, and personal healthcare compounds. Also described are methods of their administration, methods of their synthesis and manufacture, and the ionophore products of such synthesis and manufacturing methods.

19 Claims, 4 Drawing Sheets

SYNTHETIC CELLULAR MEMBRANE CHEMICAL IONOPHORE DELIVERY SYSTEM COMPRISING HEXA-AQUA LIGAND COMPOSITIONS

RELATED APPLICATION

The present application in a continuation-in-part of U.S. application Ser. No. 17/349,880 filed Jun. 16, 2021, which claims the benefit of prior U.S. Provisional Patent Application Ser. No. 63/137,088, filed Jan. 13, 2021, both of which are incorporated herein by reference.

FIELD OF THE INVENTION

The present invention relates generally to synthetic ionophores for free-ion carriage and transportation across biological membranes in vivo and, more particularly, to the use of coordination complexes of molecules with polarized hexa-aqua systems and tetra-aqua systems of free ionic metals and ionic salts as the ionophores, useful in transporting pharmaceutical and personal healthcare compounds across biological membranes in vivo to target cellular metabolic systems and thereby produce desired pharmacologic actions useful in metabolic, immunological, and other biological system disorders, and infectious disease treatment. The compositions of the invention relate to the scientific fields and subjects of inorganic & organic medicinal chemistry, redox values, pH, molecular biology, pharmacokinetics, microbiology, cellular biology, especially of mammalian cells, physiology, and physiological chemistry.

BACKGROUND OF THE INVENTION

There is a general need in pharmaceutical therapeutics for treatment regimens that have improved safety, efficacy, tolerability, improved side-effect profiles, reduced duration of action, reduced manufacturing costs, greater chemical stability, reliably repeatable batch manufacture, potential for scalability as the size of batch outputs increases, better affordability, ease of administration, accessible, lend themselves to distribution, and have extended storage life, particularly in remote geographies and in hotter or wetter climates.

There are, furthermore, global needs in pharmaceutical therapeutics for nontoxic active drug delivery systems that are designed to target biological functions with mechanisms more closely mimicking natural processes. Likewise, there are needs for active molecule delivery systems that can be applied in the fields of nutrition, and personal care, as well as in therapeutics.

In the field of infectious disease and antibiotic therapeutics, there is a need for methods of disease treatment and prevention that can build on research in understanding cellular redox reactions, both in terms of antioxidant and pro-oxidant agents acting within cells, and of research on complex ionic structures that enable (1) delivery of positive bonding, which is the action of cations, and (2) oxidative free radical effects, which is the action of anions. Redox research additionally investigates the biological roles of redox switches, and redox relays, in clinical proteomics and metabolomics to reduce oxidative and nitrosative stress on a biological system. The compounds of the invention enable and support such research.

SUMMARY OF THE INVENTION

The compounds or the invention comprise one or more of the most preferably hexa-aqua octahedral ligand configurations of metal ionic structures, or alternatively preferably tetra-aqua tetrahedral, or planar ligand configurations of metal ionic structures, or tri-aqua trihedral ligand configurations of metal ionic structures, in aqueous solution, of the general formula

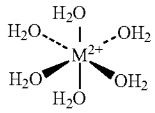

Where M is a p-block element, a d-block element, or an s-block element. At equilibrium state, there can be an alternative preferred embodiment of the invention, namely a metal tetra-aqua tetrahedral or planar ligand dihydroxy species present, which will be amine concentration-dependent and/or solution acidity-dependent. Based on anionic and cationic equilibriums, these lower-order ionic structures can configure to higher-order complex ionic structures.

In summary, the invention is a composition comprising one or more compounds selected from the group consisting of any one of $[[Zn(H_2O)_6]^{2+}]_w$, $[[Cu(H_2O)_6]^{2+}]_x$, which is an example of a hexa-aqua octahedral ligand configuration, $[[Cu(H_2O)_4]^+]_y$, which is an example of a tetra-aqua tetrahedral or planar ligand configuration, $[[Mg(H_2O)_6]^{2+}]_z$, $[HSO^-{}_4]_c$, $[NH_3]_d$, $[NH_4{}^+]_e$, $[H^+]_f$, $[SO_3{}^{2-}]_g$, $[NH_4HSO_4]_h$, and $[H_2SO_4]_j$, and mixtures thereof, wherein w, x, y, z, c, d, e, f, g, h, and j are integers that are independently greater than or equal to 0; $[H^+]$ is present as the combined molecule $H^+{\cdot}H_2O$; and the pharmaceutically or nutritionally acceptable salts, solvates, hydrates, structural isomers, and stereoisomers thereof, and is most preferably in an aqueous solution. The compositions may additionally comprise one or more compounds selected from the group consisting of any one of $[Zn(II)(H_2O)_6]^{2+}]_w$, $[Cu(II)(H_2O)_6]^{2+}]_x$, $[Cu(I)(H_2O)_4]^+]_y$, $[Mg(II)(H_2O)_6]^{2+}]_z$, $[H_3PO_4]_j$, and potassium hydrogen phthalate, and mixtures thereof, wherein: w, x, y, z, and j are integers that are independently greater than or equal to 0; $[H^+]$ is present as the combined molecule $H^+{\cdot}H_2O$; and likewise the pharmaceutically or nutritionally acceptable salts, solvates, hydrates, structural isomers, and stereoisomers thereof. In these compositions, $[NH_4HSO_4]$ may be present in a concentration of from 0.1% to 4.0% w/w, $[H_2SO_4]$ may be present in a concentration of from 0.01% to 3.0% w/w, $[Zn(II)(H_2O)_6]$ may present in a concentration of from 2.0% to 8.0% w/w, $[Cu(II)(H_2O)_6]$ may be present in a concentration of from 1.0% to 3.0% w/w, $[Mg(II)(H_2O)_6]$ may be present in a concentration of from 1.0% to 3.0% w/w, $[H_3PO_4]$ may be present in a concentration of from 0.1% to 15.0% w/w. The compositions may additionally comprise one or more compounds selected from the group consisting of hexa-aqua, tetra-aqua or tri-aqua s-block, d-block or p-block hydrates, or more preferably may additionally comprise a compound selected from the group consisting of any one of $[SeO(HO)_2]^{2+}$, which is an example of a trihedral ligand configuration metal ionic structures, $[Mn(H_2O)_6]^{2+}$, $[Ag(H_2O)_6]^{2+}$, $[Au(H_2O)_6]^{2+}$, $[V(H_2O)_6]^{2+}$, and $[Ni(H_2O)_6]^{2+}$ and mixtures thereof. Additionally, the compound potassium hydrogen phthalate may be present in a concentration of from 0.01% to 8.0%. The compositions are advantageously delivered to a patient in need thereof in a pharmaceutically acceptable formulation for administration in a form selected from the group consisting of oral, nasal, ophthalmic, otic, topical, topical administered with thermal, ultrasound, infrared, iontophoretic or radiation means, transdermal, urethral, vaginal, rectal, intravenous injection, subcutaneous injection, nebulization, and inhalation formulations. Topical formulations may be prepared at active composition concentrations of up to 30% w/w. Transdermal formulations may prepared at active composition concentrations of up to 20% w/w. Oral formulations may be prepared at active composition concentrations of up to 20% w/w. Inhalational formulations may be prepared at active composition concentrations of up to 10% w/w. Injectable formulations may be prepared at active composition concentrations of up to 5% w/w. The formulations may be prepared to have a final product pH that is in a range selected from the group of ranges consisting of a pH of less than 1.0, a pH in the range of 1.01 to 3.99, and a pH in the range of 4.00 to 5.00, and the formulation may exhibit an oxidation reduction potential of greater than 200 millivolts.

A preferred alternative embodiment of the present invention may be a composition comprising one or more compounds selected from the group consisting of any one of: $[[M(L_1)_{a1}]^{b+}]_x$, $[[M(L_2)_{a2}]^{c+}]_y$, $[[M(L_3)_{a3}]^{d+}]_z$, $[AN^{i-}]_e$, and $[CA^{g+}]_f$, and mixtures thereof, wherein: $L_1$, $L_2$, and $L_3$ are any ligand or mixed ligand comprising any one of OH, CO, $NH_3$, $H_2O$, $H_3O$, NO, $NO_2$, $NO_3$, $SO_4$, $SO_3$, $HSO_4$, NH, S, N, $NH_4$, $PO_4$, $CH_3$, $CH_2$, or $CO_2$; and mixtures thereof; M is selected from the group consisting of p-block elements, d-block elements, and s-block elements, more preferably any one of Cu, Zn, Mn, Mg, Se, Au, Ag, Vn, and Ni, and mixtures thereof; x, y, z, e, and f are independently an integer that is the number of ions forming a complex ionic structure and is greater than or equal to 0; a1 is an integer that is greater than or equal to 0 and less than or equal to 6 and is the coordination number of ligands that are coordinated to metal M; a2 is an integer that is greater than or equal to 0 and less than or equal to 6 and is the coordination number of ligands that are coordinated to metal M; a3 is an integer that is greater than or equal to 0 and less than or equal to 6 and is the coordination number of ligands to metal M; b, c, and d may be independently an integer that is greater than or equal to 0 and less than or equal to 6 and is that amount of charge that is localized on metal center M or that amount of charge delocalized around coordinate ligands; AN is an anion that is in solution, that is selected from the group consisting of the ionic forms of any one of OH, CO, $NH_3$, NO, $NO_2$, $NO_3$, $SO_4$, $SO_3$, $HSO_4$, NH, $NH_4$, $PO_4$, N, Cl, I, and Br and mixtures thereof; and CA is a cation that is in a solution consisting of a cation that is selected from the group consisting of the ionic forms of any one of H, Ca, Na, Fe, K, Mg, Mn, Zn, Cu, Li, or mixtures thereof, and a s-block element, a p-block element, or a d-block element, and mixtures thereof, and the pharmaceutically or nutritionally acceptable salts, solvates, hydrates, structural isomers, and stereoisomers thereof.

The invention further comprises a method of administering the compositions disclosed herein for treating a disease, comprising the step of administering to a mammal in need thereof an aqueous ionic mineral complex comprising an ionic metal bonded to a plurality of $H_2O$ ligands to form a metal-ligand complex, the $H_2O$ ligands enabling transport of the metal-ligand complex through the human patient to a cellular target affected by over-production of superoxide ion, said metal-ligand complex selected from the group consisting of any one of $[[Zn(H_2O)_6]^{2+}]_w$, $[[Cu(H_2O)_6]^{2+}]_x$, $[[Cu(H_2O)_4]+]_y$, $[[Mg(H_2O)_6]^{2+}]_z$, $[HSO^-{}_4]_c$, $[NH_3]_d$, $[NH_4{}^+]_e$, $[H^+]_f$, $[SO_3{}^{2-}]g$, $[NH_4HSO_4]_h$, and $[H_2SO_4]_j$, and mixtures thereof, wherein: w, x, y, z, c, d, e, f, g, h, and j are integers that are independently greater than or equal to 0; and $[H^+]$ is present as the combined molecule $H^+ \cdot H_2O$; and the pharmaceutically or nutritionally acceptable salts, solvates, hydrates, and structural or stereometric isomers thereof, and may further comprise a compound selected from the group consisting of $[Zn(II)(H_2O)_6]^{2+}]_w$+$[Cu(II)(H_2O)_6]^{2+}]_x$, $[Cu(I)(H_2O)_4]^+]_y$, $[Mg(II)(H_2O)_6]^{2+}]z$, $[H_3PO_4]_j$, and potassium hydrogen phthalate, and mixtures thereof, wherein w, x, y, z, and j are integers that are independently greater than or equal to 0; and $[H^+]$ is present as the combined molecule $H^+ \cdot H_2O$; and the pharmaceutically or nutritionally acceptable salts, solvates, hydrates, structural isomers, and stereoisomers thereof, and in particular may be administered for a purpose selected from the group consisting of medical diagnosis, detection of anaerobic cells in a biological system, medical treatment, personal care, cosmetic purposes, and nutritional supplementation.

Also disclosed and claimed within the scope of the present invention are the pharmaceutically acceptable salts, hydrates, solvates, structural isomers, and stereoisomers thereof.

The compositions of the invention are intended to be used in human and veterinarian patients, in the fields of allopathic, osteopathic, homeopathic, and naturopathic medicine.

DETAILED DESCRIPTION OF THE INVENTION

Figure 1:
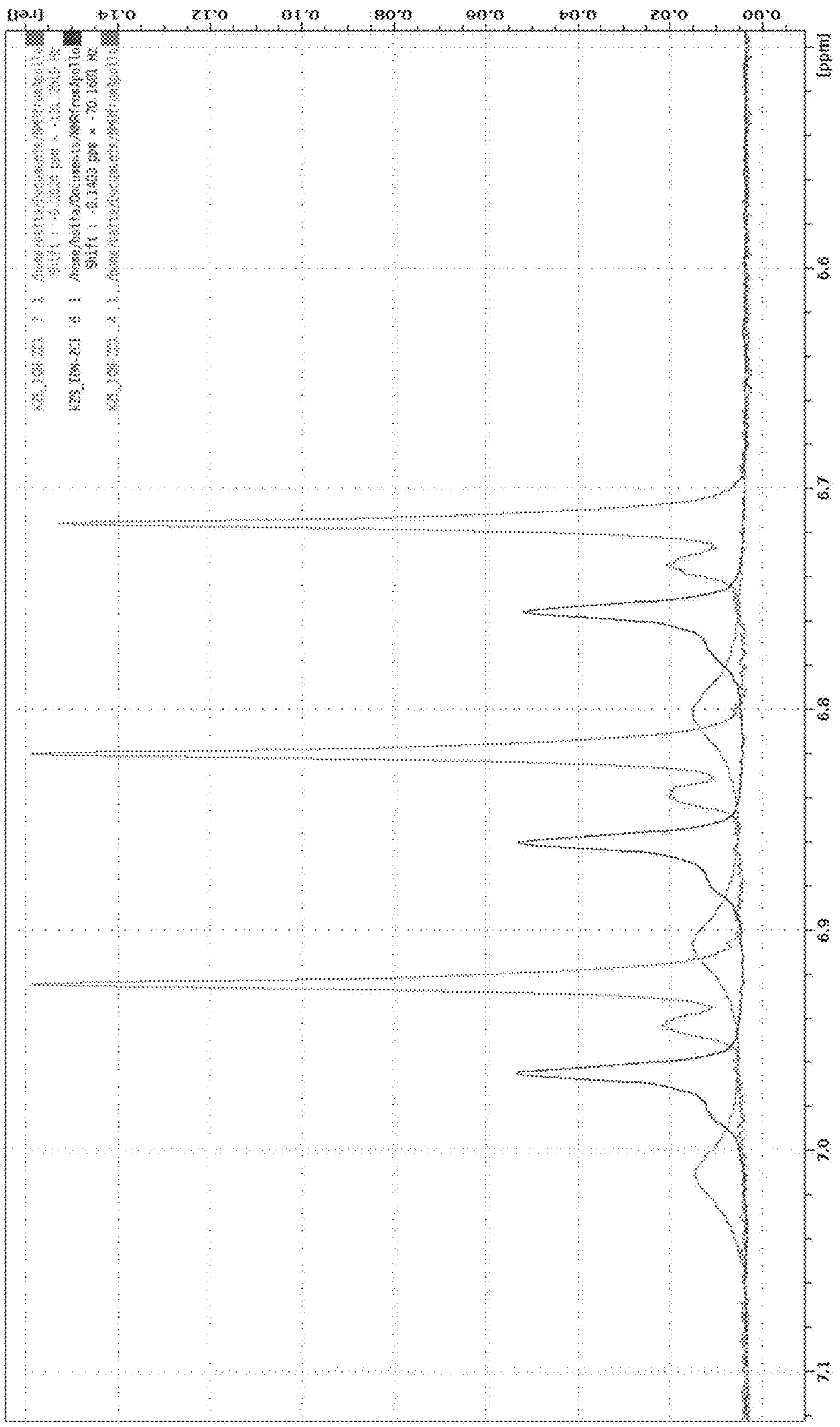
FIG. 1 is an $^1$H-NMR spectrum generated at Watergate $^1$H-NMR spectra of red: 275K, spectra blue: 298K, and spectra green: 320K temperatures.

The present invention in its varying embodiments will now be described more fully This invention may, however, be embodied in many different forms and should not be construed as being limited to the embodiments set forth herein. Rather, these embodiments are provided so that this disclosure will be thorough and complete, and will fully convey the scope of the invention to those skilled in the art.

Redox Signaling-RSS, RNS, and ROS Modes of Action. Redox balance is the underlying chemical mechanism for all biological processes. Biological homeostasis is created, regulated, and sustained by reduction-oxidation (redox) reactions that drive photosynthesis, respiration, and most other biological reactions necessary for biological systems to function. Oxidative stress is thought to account for aberrant redox homeostasis and contribute to aging and disease. However, often, administration of antioxidants to address oxidative stress is ineffective, suggesting that our current understanding of the underlying regulatory processes is incomplete. Miriam M. Cortese-Krott, A. K. (2017 Oct. 1). The Reactive Species Interactome: Evolutionary Emergence, Biological Significance, and Opportunities for Redox Metabolomics and Personalized Medicine. Antioxidants & Redox Signaling, 27(10). https://doi.org/10.1089/ars.2017.7083

Key to the manipulation of many biological mechanisms to restore normal biological function, are the normal functioning of redox systems consisting of chemical interactions of one or all the following reactive species: Reactive Oxygen Species (ROS), Reactive Nitrogen Species (RNS), and Reactive Sulfur Species (RSS). Olson, K. R. (2020 Feb. 26). Reactive oxygen species or reactive sulfur species: why we should consider the latter. *Journal of Experimental Biology* 2020, p. 223. Retrieved 2021 from https://jeb.biologists.org/content/223/4/jeb196352. These species play a dual role as capable of being both toxic compounds, when unbalanced, and beneficial compounds, when balanced. The delicate balance between their two antagonistic effects is clearly an important aspect of life. Lien Ai Pham-Huy, H. H.-H. (2008, June). Free Radicals, Antioxidants in Disease and Health. *International Journal of Biomedical Sciences,* 4(2), 89-96. Retrieved 2021 from https://www.ncbi.nlm.nih.gov/pmc/articles/PMC3614697/. The present invention disclosed herein confirms that the presence of the elements of oxygen, nitrogen, and sulfur, in their respective forms as reactive species, are potentially involved in the targeting of both redox signaling processes in metabolic pathways, and in targeting key metabolic intermediates. These reactive species provide multiple cellular signaling pathways, redox systems, and electron transfers for homeostasis.

Reactive Oxygen Species—ROS Cationic hydrogen ($H^+$ (aq)) is an electron donor (reduction) for hydroxyl radical (HO·) or radical oxygen ($O_2^-$), and is also known as a factor, when overabundant, in oxidative stress, cell aging (truncated telomere length), and DNA methylation.

Reactive Nitrogen Species—RNS Cationic metal amine complex ($NH_4^+$ (aq)) is an electron donor for nitrogen reduction, and/or acts as an ammonia ($NH_3$) ligand in triggering glutamate production, used in amino acid synthesis. Oxidative stress is a well-established phenomenon that occurs in neurodegenerative disease. This, coupled with an increase in apoptosis and autophagy, contributes to the neurodegeneration and memory loss observed in Alzheimer's disease, Parkinson's disease, and amyotrophic lateral sclerosis. Overabundance of reactive oxygen and nitrogen species are highly abundant in these disorders. New antioxidant and mitochondrial-based therapies aimed at such imbalance show promise to reduce neuronal cell loss and promote neuroprotection, which will have a positive effect on patient outcomes. Sergio Di Meo, T. T. (2016, July 12). Role of ROS and RNS Sources in Physiological and Pathological Conditions. *Oxid Med Cell Longev,* 1245049. https://dx.doi.org/10.1155%2F2016%2F1245049.

Reactive Sulfur Species—RSS Anionic Sulfur ($HSO_4^-$ (aq)) triggers redox switches and redox relays. Sulfur is considered a part of cellular antioxidant systems, and there is mounting evidence that RSS imbalance has stressor-like properties similar to the ones found in ROS imbalance, but that they are formed under certain conditions as a separate class of oxidative stressors. Arno R. Bourgonje, M. F. (2020). Oxidative Stress and Redox-Modulating Therapeutics in Inflammatory Bowel Disease. *Science Direct,* 26(11), 1034-1046. https://doi.org/10.1016/j.molmed.2020.06.006.

Metabolic Activities. More specifically, there is a need for achieving a non-toxic delivery system to the cell that provides preventative or therapeutic uses of metal cations that are carried to a site of action. The compositions of the present invention meet this need by the utilization of aqua ligand bonds, preferably hexa-aqua ligand or tetra-aqua ligand moieties, and most preferably, hexa-aqua ligand moieties, that can effectively protect such metal cations from being immediately bonded with the first available anions, and thus enabling polarity movement between and within living cells. Such aqua ligand bond-enabled moieties comprising the compositions of the invention can exploit the distinct differences between (1) aerobic cells, whether they are continuing a process toward apoptosis, or whether they are changing toward a mutated state, and (2), anaerobic cells, whether they are in a pathogenic or cancerous state, in their respective different aerobic versus anaerobic behaviors in glycolysis, the citric acid cycle, cellular respiration, or the electron transport chain.

Anaerobic processes do not require oxygen, while aerobic processes do require oxygen. The use of oxygen is directly involved in the citric acid cycle because it is an aerobic process. The compositions of the invention sustain this process through positive hydrogen electron donation resulting in a proton, $H^+$, in the form of a hydronium ion, $H_3O^+$. Creating and keeping a hydronium ion equilibrium concentration is an essential factor when dealing with chemical reactions that occur in aqueous solutions of the compositions of the invention. The hydronium ion's concentration relative to hydroxide is a direct measure of the pH of a given solution. The hydronium ion is formed when a protonic acid is present in water. The compositions of the invention contribute to the removal of high-energy electrons from bioavailable carbon fuels. These high-energy electrons reduce $O_2$ to generate a proton ($H^+$) gradient which is used to synthesize adenosine triphosphate (ATP). The reduction of $O_2$ and the synthesis of adenosine triphosphate (ATP) constitute oxidative phosphorylation.

Glycolysis. Glycolysis occurs in all living cells and is believed to be one of the first types of respiration to have evolved in anaerobic cells (by some estimates, for billions of years, before the metabolic utilization of oxygen). Glycolysis occurs in the cell's cytoplasm, and glycolysis precedes the citric acid cycle. The process of glycolysis requires the use of two adenosine triphosphate (ATP) molecules. ATP, which constitutes a molecular metabolic currency, is advantageously boosted through the present invention's transport assistance of metal cations as a part of nutrient uptake. When glucose is broken down from a six-carbon sugar molecule into two three-carbon sugar molecules of pyruvate, then four ATP and two NADH (reduced nicotinamide adenine dinucleotide) molecules are created. NADH is transported to the citric acid cycle to create more ATP under aerobic conditions. If no oxygen is present, pyruvate is not allowed to enter the citric acid cycle, and it is further oxidized to produce lactic acid. Fermentation and oxidative stress ($O_2$) are both created by cells functioning anaerobically and promote the continuation of an anaerobic cell environment. A formulation comprising the compositions of the invention reduces this stress by utilizing available hydrogen ($H^+$) cation donated by the invention's aqua-ligand ionic species or mixed hydroxyl/aqua ligand ionic species.

Citric Acid Cycle. The citric acid cycle constitutes the first stage in cellular respiration, removing high-energy electrons from carbon fuels. These electrons reduce $O_2$ to generate a proton gradient ($H^+$) used to synthesize ATP. The reduction of $O_2$ and the synthesis of ATP constitute oxidative phosphorylation. The compositions of the invention can donate $H^+$ and $O_2$ electrons directly into the electron transport chain, thereby facilitating the function of the citric acid cycle, and reducing an anaerobic cell environment properly. The citric acid cycle takes place in the matrix of the mitochondria. It is a series of chemical reactions and electron transfers used by all aerobic organisms to generate energy. If oxygen is not present, the respiratory cycle cannot function, which shuts down the citric acid cycle, potentially initiating anaerobic cell metabolism. When NAD+ is not in production, the relative ratio of NADH to NAD+ increases, which causes glycolysis to produce lactic acid instead of pyruvate, a required component of the citric acid cycle. The citric acid cycle is heavily dependent on oxygen, deeming it an aerobic process.

Electron Transport Chain. When NADH is reduced to NAD, an electron transport chain accepts the electrons from the molecules. As the electrons are transferred to each carrier within the electron transport chain, free energy is released and is used to form ATP. Oxygen is the final acceptor of electrons in the electron transport chain. Without oxygen, the electron transport chain becomes overloaded with electrons, reducing or eliminating functionality. The compositions of the invention can transfer electrons through utilizing natural electron donors via redox reactions across a cell membrane, acting at the atomic level and positively altering a dysfunctional electron transfer chain.

Mitochondrial Function. Metabolic processes, and the multiple enzymes that enable them, occur within the mammalian mitochondrion, and include β-oxidation of fatty acids, the urea cycle, the citric acid cycle, and ATP synthesis, each of which are respectively vital for many metabolic pathways in the cell. There is a need for the identification of new reactive species involved in such intracellular redox signaling and new redox pathways to address diverse dietary and medical interventions. The compounds of the present invention enable the identification of such new reactive species. The equilibrated interplay and proper balance between specific micronutrients at the cellular level is necessary in the reduction of illness and disease. Establishing biological homeostasis through corrective mitochondrial metabolism is a highly cost-effective method of disease prevention. The compounds of the invention can assist in the control of disease and of health problems through their actions in achieving balanced redox processes. Persistent physical impairment of cellular redox processes occurs before and after critical illness, and recent clinical data points towards mitochondrial dysfunction as an essential determinant of this problem. The prime targets of redox modulators are generally small molecule "reactive species" such as ROS, RNS, and RSS. The biological impact and the underlying chemistry of these reactive, often inorganic species provides a holistic view of redox control.

Anticancer Activities. One of the modes of action of the compositions of the present invention is that they target cancer cells by apoptosis. Clinical studies on several human cancer cell types have used the cell's natural death mechanism as an anticancer therapy. Treating an afflicted biological system to enhance the natural function of apoptosis to prevent or treat cancer is an activity of the compositions of the present invention. The activities of superoxide dismutase (SODs) are often lowered during early cancer development, making it a rational candidate target for cancer therapeutic intervention. Animal studies have now shown that the compositions of the present invention exhibit anticancer activity by activating an apoptotic pathway.

Exploiting the natural mechanisms for cell death is a highly effective method of treatment. Drugs targeting apoptosis are some of the most successful non-surgical treatments. Some have proven efficacy in all cancer cells as apoptosis evasion is a cancer hallmark, but they come at the cost of having high cytotoxicity. See Singh, C. M. (2018 Feb. 2). Apoptosis: A Target for Anticancer Therapy. (C. College, Ed.) *International Journal of Molecular Science* (Department of Biology, Division of Natural & Social Sciences), 2, https://dx.doi.org/10.3390%2Fijms19020448. The compositions of the present invention create apoptotic signals in several forms through the actions of cationic metal delivery, Zn/Cu SOD, redox signaling, and reduction of free radicals. All these modes of action contribute to change the tumor environment through cell death induced by the extracellular signals produced by the compositions of the invention.

Reactive oxygen species (ROS) are increasingly recognized as critical determinants of cellular signaling and a strict balance of ROS levels must be maintained to ensure proper cellular function and survival. Brandon Griess, E. T. F. (2017 Aug. 24). Extracellular Superoxide Dismutase and its Role in Cancer. *Free Radic Biol Med,* 1. https://dx-.doi.org/10.1016%2Fj.freeradbiomed.2017.08.013. Cancer cells switch their metabolism to glycolysis to meet their energy requirements, known as the Warburg effect. One of the anticancer activities of the compositions of the present invention is that they can exploit the Warburg effect to push the cancer cell further into the cellular respiration process, thereby creating an apoptotic death.

Antimicrobial Modes of Action. Multiple studies support the antimicrobial efficacy of the compositions of the present invention, as are specifically described and disclosed below. Anaerobic cells may be clinically induced to experience cytosolic metal intoxication from the overload of natural metal cations that can be measuredly delivered by compositions of the present invention, causing necrotic and or apoptotic (programmed) cell death. Lee, S. Y. (2018 Jan. 31). Regulation of Tumor Progression by Programmed Necrosis. (R. Franco, Ed.) *Hindawi* (Oxidative Medicine and Cellular Longevity), 2. https://doi.org/10.1155/2018/3537471. This method of cell death triggers several immune responses in biological system. Ine Jorgensen, M. R. (2017 Jan. 31). Programmed cell death as a defense against infection. Nat Rev Immunol, 151-164. https://dx.doi.org/10.1038%2Fnri.2016.147. A non-toxic essential metal (for example as found in nutrients) uptake by aerobic cells during cellular respiration, and apoptotic cell death for anaerobic cells, creates an environment that prevents the adverse cascading events toward pathogen-induced disease. Pete Chandrangsu, C. R. (2017 Mar. 27). Metal Homeostasis and Resistance in Bacteria. *Nat Rev Microbiol,* 338-350. https://doi.org/10.1038/nrmicro.2017.15. Research has shown that zinc and copper ions can also induce oxidative reactions, inactivation of viral infection proton channels, or viral membrane destabilization, all activities that can be ascribed to the compositions of the present invention. Vikram Gopal, B. E.-P.-s. (2021 Jan. 6). Zinc-embedded fabrics inactivate SARS-CoV-2 and influenza A virus. (bioRxiv, Ed.) *bioRxiv,* 1-27. https://dx.doi.org/10.1101%2F2020.11.02.365833.

Accordingly, a need exists for a solution to at least one of the aforementioned challenges. More specifically, a need exists for a chemical means for carriage and transport of free ions across biological membranes in vivo.

Features, Objects, and Advantages of the Compositions of the Present Invention

The concentrated iontophoretic metal ion delivery system of the present invention as disclosed herein, includes compositions comprised of one or more active ionophore moieties, pharmaceutical formulations of such active moieties compounded with pharmaceutically acceptable excipients, methods of making such moieties, compositions, and formulations, and methods of administering such formulations in the prevention and treatment of diseases. Multiple administration methods and dosing levels provide a spectrum of safety profiles that target tumor environments, tumor areas in all age groups, and concurrent treatments. These compositions, formulations, methods of preparation, and methods of administration address the aforementioned needs.

Activities of the compositions of the present invention include the following non-limiting exemplary list: promoting increased production of superoxide dismutase; preventing formation of free radicals; mitigating levels of free radicals; increasing and improving the antioxidant capacity of a biological system; reducing levels of oxidative stress; protecting a biological system from overproduction of, and reducing & detoxifying existing levels of, reactive oxygen species, reactive nitrogen species, and reactive sulfur species; reducing levels of prooxidants; addressing deficiencies of enzymatic and non-enzymatic antioxidants; antagonizing superoxide overproduction; supporting normal mitochondrial function and normal ATP biosynthesis; decreasing the ratio of NADH to NAD+; raising levels of apoptosis; and constituting anti-pathogen direct toxins.

Acidic pH. A key feature of the compositions of the present invention in all of its various pharmaceutical formulations is that they register very low pH levels of from 0.2 to 4.0, and most preferably 2.0, which not only acts to increase their delivery efficiency and therapeutic efficacy, but which also show, surprisingly and unexpectedly, limited or no adverse reactions in biological systems at such low pH levels.

It is a feature of any given preferred embodiment of the present invention that it contains a high level of one or more of free sulfur, amine, sulfate ions, metal hexa-aqua structures, metal tetra-aqua structures, metal hydroxyl/aqua mixed ligand species, and hydronium ion, which can be transported to the various targeted locations in a biological system through micro or macro circulatory transport, and respectively work to balance reactive oxygen species, reactive nitrogen species, and reactive sulfur species, that are involved in cell signaling, protein actions, and the multiple balances of the metabolic cell cycle.

Delivery of High Levels of $H^+$. Compositions of the present invention deliver high levels of H+, having pH's at 1.0 or below 1.0, and may be characterized as carrying $H^+$ in a $Zn^{2+}$ $Cu^{2+}$ superoxide dismutase (SOD) ligand. There are many unknown beneficial potentials for the technology of the present invention, based on the processes and relationships of the invention's preferred compositions with ROS, RNS, RSS, and the interactions with NOx, $H_2S$, and $O_2$, and their derived species. The core non-metal components of preferred embodiments of the present invention, $NH_3$, $HSO_4^-$, and $H^+$, influence and modulate levels of each of the above reactive species by chemical mechanics, electron transfer, or biological processes. Gopi K. Kolluru, X. S. (2020 Mar. 5). Reactive Sulfur Species—A New Redox Player in Cardiovascular Pathophysiology. (T. a. Arteriosclerosis, Ed.) *Arteriosclerosis, Thrombosis, and Vascular Biology*. https://doi.org/10.1161/ATVBAHA.120.314084.

Superoxide Dismutase (SOD) Production. Natural forms of SOD and their prior art delivery methods are difficult to manufacture, hard to reproduce, and expensive. In contrast, the artificial SOD produced by the present invention can be produced in large quantities and utilized in several application technologies such as creams, injectables, transdermal patches, inhalers, and other administration methods currently used by health practitioners. Compositions of the present invention in their SOD forms can be further developed with manganese, as $Mn^{2+}$ SOD and iron, as $Fe^{2+}$ SOD, as ionic metals in addition to the $Zn^{2+}/Cu^{2+}$ SOD described above. Zinc is a redox-inert metal, that is, it functions as an antioxidant through the catalytic action of copper/zinc-superoxide dismutase, stabilization of membrane structure, protection of protein sulfhydryl groups, and upregulation of the expression of metallothionein, (which itself possesses a metal-binding capacity and exhibits antioxidant function. Lee, S. R. (2018 Mar. 20). Critical Role of Zinc as Either an Antioxidant or a Prooxidant in Cellular Systems. (G. Gobe, Ed.) Hindawi. https://www.hindawi.com/journals/omcl/2018/9156285/. Preferred embodiments of the compositions of the invention comprise or support the production of artificial SOD in biological systems. Preferred compositions containing and delivering suitable metals will support the production of natural SOD enzymes with the canonic role of oxygen radical enzymatic dismutation. Multiple studies support the need for SOD balances in biological systems in order to prevent and mitigate free radicals. These radicals affect the functionality of the immune system and are frequently a precursor to mutations and disease. Superoxide dismutase is widespread in the human body, including the skin of the trunk and of the appendages. Giovanna G. Altobelli, S. V. (2020, May 12). Copper/Zinc Superoxide Dismutase in Human Skin: Current Knowledge. (F. i. Medicine, Ed.) *Frontiers in Medicine,* 1. https://doi.org/10.3389/fmed.2020.00183.

Members of the SOD family are found in several preferred embodiments of the invention. SOD has been studied in different models since the discovery of its involvement in ALS disease, a disease in which mechanisms of prion-like protein misfolding and pathology propagation are known to play roles in ROS generation, with subsequently-caused extensive damage to SOD. A strategy in administration of compositions of the invention is to serve as an effective antioxidant, and to neutralize a radicalized SOD1 with a synthetic SOD delivered via a carrier compound of the invention. An early-stage trial of an investigational therapy for amyotrophic lateral sclerosis (ALS) suggests that people could tolerate the experimental drug that is a preferred embodiment of the invention, and in exploratory results, the experimental drug was linked to possible slower progression in people with a genetic form of the disease that was caused by mutations in a gene called the superoxide dismutase gene SOD1 on chromosome 21. American Academy of Neurology. (2019, May 1). Experimental drug shows promise for genetic form of ALS. (S. News, Ed.) *Science News*, p. 1. Retrieved 2021 from https://www.sciencedaily.com/releases/2019/05/190501161224.htm.

Copper/Zinc Superoxide Dismutase (Cu/Zn SOD) is an important enzyme that has elicited significant interest among medicinal chemists. Zinc is a redox-inert metal, and it functions as an antioxidant through the catalytic action of copper/zinc superoxide dismutase, stabilization of membrane structure, protection of protein sulfhydryl groups, and upregulation of the expression of metallothionein. See Paolo Mondola, S. D. (2016). The Cu, Zn Superoxide Dismutase: Not Only a Dismutase Enzyme. *Frontiers in Physiology,* 1. https://doi.org/10.3389/fphys.2016.00594. Manganese Superoxide Dismutase (MnSOD) enzyme helps protect and reinforce the mitochondrial and biological functions. The mechanism by which MnSOD protects cells from the harmful effects of overproduction of reactive oxygen species (ROS) and the effects of ROS on mitochondrial metabolic enzymes is not yet known. A preferred composition of the invention that contains the manganese metal ion will beneficially mimic and/or increase the production of MnSOD enzymes. MnSOD converts superoxide anions to hydrogen peroxide plus oxygen, providing the first line of defense against oxidative stress in mitochondria. Heart mitochondria are known to exhibit higher MnSOD activity than liver mitochondria. In mitochondria from both tissues MnSOD activity decreased after incubation at low oxygen concentration (hypoxic mitochondria). The effects of free $Ca^{2+}$ ($[Ca^{2+}]_f$) and free $Mg^{2+}$ ($[Mg^{2+}]_f$) on normoxic and hypoxic mitochondria from either organ were tested. In normoxic mitochondria from either tissue, both $[Ca^{2+}]_f$ and $[Mg^{2+}]_f$ activated the enzyme, although $[Mg^{2+}]_f$ was less efficient as an activator and the effect was lower in heart than in liver mitochondria. When added simultaneously, high $[Ca^{2+}]_f$ and $[Mg^{2+}]_f$ exhibited additive effects which were more pronounced in heart mitochondria and were observed regardless of whether mitochondria had been incubated under normal or low oxygen. The data suggest that $[Ca^{2+}]_f$ plays a role in regulating MnSOD in concert with the activation of aerobic metabolism. Pérez-Vázquez, V., Ramírez, J., Aguilera-Aguirre, L. et al. Effect of Ca2+ and Mg2+ on the Mn-superoxide dismutase from rat liver and heart mitochondria. Amino Acids 22, 405-416 (2002). Retrieved in 2021 from https://doi.org/10.1007/s007260200024

H+ As An Antioxidant. The cationic hydronium component that is present in preferred embodiment compounds of the invention can donate hydrogen from the ligand complex to an $O_2^-$ radical, acting as a powerful antioxidant to reduce oxidative stress and the related diseases caused by such stress. Oxidative stress can be defined as excess production of reactive oxygen/nitrogen species (ROS/RNS) as prooxidants and/or a deficiency of enzymatic and nonenzymatic antioxidants, which are involved in the detoxification of ROS/RNS.

SOD and Anaerobes. SOD can also eliminate certain anaerobic diseases present, including any living disease associated with protein bound beta-N-Methyl Amino-L-Alanine (BMAA) associated with neurodegeneration in subjects. Superoxide dismutase in the extracellular space has unique characteristics and functions in cellular signal transduction, showing anti-cancer properties. Preferred compositions of the invention create an artificial in situ SOD that can be administered and utilized to treat superoxide overproduction. The metallic form of such an artificial SOD can increase the concentration of the natural enzymatic form of SOD by re-balancing deficiencies of metal ions that are needed in the production of SOD enzymes, to thereby increase a positive level of biological function. The compositions of the invention therefore may be used in treating deficiencies in the production of SOD enzymes, rebalancing levels of SOD, and neutralizing radical SOD, all to reestablish normalcy in biological systems.

Prevention of disease. Another goal of the invention is to aid in the prevention of disease, through preventing metabolic disturbances in biological systems, treating cells at the atomic level directed towards balanced mitochondrial harmony, reducing free radicals arising from environmental stress, toxicities, and the eventual mutations they cause. Synergy between the elements occurs largely on a metabolic level. The invention can be developed into specific formulations that aid in prevention of disease through rebalancing of the biological system by the application of stimulant or sedative pharmacological substances. With a better understanding and application of these concepts, a more comprehensive approach to health care can be realized, thus avoiding the necessities of a nutritional version of roulette that is described in the literature. Specially individualized administration of known stimulants and sedatives to individual treatment regimens may then lead to improved responses with fewer undesirable side effects. Watts, David L. (1990 Jan. 1). Nutrient Interrelationships Minerals—Vitamins—Endocrines, Journal of Orthomolecular Medicine Vol. 5, No. 1, 1990. Retrieved 2021 from http://orthomolecular.org/library/jom/1990/pdf/1990-v05n01-p011.pdf.

Gastrointestinal Absorption. The synthesized ionophores of the invention are compounds that can safely target low absorbency deficiencies and provide a soluble mineral delivery means in all administration methods. Biological systems must break down food firstly into its nutritional components, and this is typically done in the digestive system. Many types of foods effectively reduce nutritional absorption, create antagonistic nutritional imbalances, and destroy critical processes in the biology of the gut. Formulations of the invention solve this problem by carrying and providing a highly bioavailable soluble nutrient in water, it being bioavailable directly to the cellular environment where needed in the subject. This delivery system thereby circumvents the variables of the digestive system process, such as gut maladies, pathologies and diseases, gut energy requirements, patient age, and gastrointestinal tract absorbance issues. Any impairment of the gastrointestinal (GI) tract can increase the risk of developing infectious, inflammatory, and dysfunctional GI processes, ultimately reducing drug delivery, nutritional absorbency, and/or the uptake of one nutrient and not another, thus creating an imbalance in the biological system. Administration methods of the invention provide an alternative to oral supplementation and a targeted approach to nutritional delivery. Appropriate physiological function requires optimal nutrition, which needs to be in balance in order to prevent potential detrimental interactions, especially when administered at typical pharmacological dosages. Many nutrients function in harmony to complement digestive function and assimilation. Some nutrients may hinder these processes and compete for uptake, while others may also be required in tandem to assist in metabolism which may ultimately affect several biochemical cycles. Schoendorfer, Niikee (2012 Jan. 1). Micronutrient interrelationships: Synergism and antagonism, JOUR, 159. Retrieved 2021 from https://www.researchgate.net/publication/286184266 Micronutrient_interrelationships_Synergism_and_antagonism.

Adequate nutrient levels are essential for mitochondrial function as several specific micronutrients play crucial roles in energy metabolism and ATP-production. E. Wesselinka, W. K. (2018 Aug. 31). Feeding mitochondria: Potential role of nutritional components to improve critical illness convalescence. (Elsevier, Ed.) *Elsevier,* 38(3), 982-995. Retrieved 2021 from https://www.sciencedirect.com/science/article/pii/S0261561418324269. Nutritional disease or nutrient-related diseases are conditions that cause illness in humans, and they can be treated with compositions of the invention. Such diseases may include dietary deficiencies or excesses, obesity, eating disorders, and chronic diseases such as cardiovascular disease, hypertension, cancer, and diabetes mellitus. Weininger, J. (2021, November 11). *Nutritional disease*. (Britannica, Editor, Britannica, Producer, & Britannica) Retrieved 2021 from: https://www.britannica.com/science/nutritional-disease.

Nutrient Supplementation. The compositions of the invention allow for personalized approaches in administration methods and dosing to establish a homeostatic state in a biological system. Oxidative stress occurs when the levels of reactive species surpass the antioxidant capacity of the organism. In low nutritional absorbency conditions, the role of gut health and food sources become magnified and relatively small deficiencies may then have a detrimental effect on nutritional balances. For example, magnesium Mg deficiency can go unnoticed even after a blood test shows it as being in an average range. Serum Mg does not reflect intracellular Mg, the latter making up more than 99% of total body Mg. Most cases of Mg deficiency are undiagnosed. Mg deficiency correlates with the formation of many different diseases and is a common occurrence in many diets. For example, adipose tissue is considered an endocrine organ that promotes excessive production of reactive oxygen species when in excess, thus contributing to lipid peroxidation, and magnesium deficiency is now known to contribute to the development of oxidative stress in obese individuals, as this mineral plays a role as an antioxidant, participates as a cofactor of several enzymes, maintains cell membrane stability, and mitigates the effects of oxidative stress. Studies show that obese subjects have low serum concentrations of magnesium, as well as high concentrations of oxidative stress markers in these individuals Morais, J. B. S., Severo, J. S., Santos, L. R. d. et al. Role of Magnesium in Oxidative Stress in Individuals with Obesity. Biol Trace Elem Res 176, 20-26 (2017). Retrieved 2021 from: https://doi.org/10.1007/s12011-016-0793-1. Furthermore, it is evident that adequate intake of magnesium contributes to its appropriate homeostasis in the body. Thus, there is a need for intervention with supplementation of this mineral for the prevention and treatment of disorders associated with this chronic disease. The compositions of the invention can be developed to address specific nutritional deficiencies, toxicities, and multi-complexes to prevent and create nutritional homeostasis in a biological system. As an example, with $Mg^{2+}$ a maximal increase in Mn-SOD activity was obtained in the presence of 1.5 mM [$Mg^{2+}$]. Pérez-Vázquez, V., Ramírez, J., Aguilera-Aguirre, L. et al. Effect of $Ca^{2+}$ and $Mg^{2+}$ on the Mn-superoxide dismutase from rat liver and heart mitochondria. Amino Acids 22, 405-416 (2002). https://doi.org/10.1007/s007260200024. The compositions of the invention comprise highly bioavailable nutritional supplement carriers, incorporating all forms and ratios of essential minerals, vitamins, and deliver all other nutrition benefits through the digestive tract, topical, nasal, intravenous, or nebulized routes, and/or by oral ingestion. The compositions of the invention increase levels of essential transitional metals in the skin, lymph fluids, interstitial or extracellular fluids, blood, or cells. Nutritional balancing can be achieved through the synergistic or antagonistic effects of essential minerals, vitamins, and managing deficiencies or toxicities through ratios within the invention, as has been done with Zn and Cu as an example. Additionally, they can be used for the reduction of Oxidative Stress and used in ketogenesis as a ketogenic set of reactions that aim to regain energy released in ketolysis via oxidation of ketone bodies, and they can furthermore be used as a biocatalyst in clinical or nutritional metabolomics.

Health Adjunctive Aid. Another goal of the invention is to support the capacity to treat metabolic imbalances and deficiencies, toxicities, pathogens, and mutations prior to the diagnosis of a disease, i.e. to act as a preventative measure. As an example, zinc can widely adjust energetic metabolism and is essential in restoring the impaired energetic metabolism of cellular physiology. Studies show that obese subjects have low serum concentrations of magnesium as well as high concentrations of oxidative stress markers. Furthermore, it is evident that an adequate intake of magnesium contributes to its appropriate homeostasis in the body. Morais, J. B. S., Severo, J. S., Santos, L. R. d. et al. Role of Magnesium in Oxidative Stress in Individuals with Obesity. Biol Trace Elem Res 176, 20-26 (2017). https://doi.org/10.1007/s12011-016-0793-1. Zinc enhances the cellular energy supply to improve cell motility and restore impaired energetic metabolism in a toxic environment induced by OTA. (S. Reports, Ed.) *Scientific Reports,* 7, 14669. https://doi.org/10.1038/s41598-017-14868-x. The high safety profile of the compositions of the invention allows for long-term preventive dosing in all biological systems of all ages. The compositions of the invention can be designed for nutritional purposes to be delivered by all types of administrative methods and routes. These methods can be administered locally or delivered systemically to circumvent poor gut health and nutritional absorbency issues. The compositions in topical applications protect the skin, the largest organ of the body, from the free radicals arising out of environmental stress.

Treatment of Cancer. The next major goal and feature of the compositions of the invention is directed to addressing the treatment of cancer. Cancers include Actinic keratoses (Aks), Acute Lymphoblastic Leukemia (ALL), Acute Myeloid Leukemia (AML), Adrenal gland tumors, Anal cancer, Basal cell carcinoma, Bile duct cancer, Bladder cancer, Blood cancers, Bone cancer, Bowel cancer, Brain tumors, Breast cancer, Cancer of Unknown Primary (CUP), Cancer metastasis to bone, Cancer metastasis to brain, Cancer metastasis to liver, Cancer metastasis to lung, Carcinoid, Cervical cancer, Children's cancers, Chronic Lymphocytic Leukemia (CLL), Chronic Myeloid Leukemia (CML), Colorectal cancer, Ear cancer, Endometrial cancer, Eye cancer, Follicular dendritic cell sarcoma, Gallbladder cancer, Gastric cancer, Gastro-esophageal junction cancers, Germ cell tumors, Gestational Trophoblastic Disease (GTD), Hairy cell leukemia, Head and neck cancer, Hodgkin's lymphoma, Kaposi's sarcoma, Kidney cancer, Large bowel and rectal neuroendocrine tumors, Laryngeal cancer, Leukemia, Linitis plastica of the stomach, Liver cancer, Lung cancer, Lung Neuroendocrine Tumors (NETs), Lymphoma, Malignant schwannoma, Mediastinal germ cell tumors, Melanoma skin cancer, Men's cancer, Merkel cell skin cancer, Mesothelioma, Molar pregnancy, Mouth and oropharyngeal cancer, Myeloma, Nasal and paranasal sinus cancer, Nasopharyngeal cancer, Neuroblastoma, Neuroendocrine Tumors, Neuroendocrine Tumors of the pancreas, Non-Hodgkin lymphoma, Non-Hodgkin lymphoma in children, Esophageal cancer, Ovarian cancer, Pancreatic cancer, Penile cancer, Persistent trophoblastic disease and choriocarcinoma, Phaeochromocytoma, Prostate cancer, Pseudomyxoma peritonei, Rare cancers, Rectal cancer, Retinoblastoma, Salivary gland cancer, Secondary cancer, Signet cell cancer, Skin cancer, Small bowel cancer, Small bowel Neuroendocrine Tumors (NETs), Soft tissue sarcoma, Stomach cancer, Stomach Neuroendocrine Tumors (NETs), Squamous cell carcinoma, Testicular cancer, Thymus gland tumors, Thyroid cancer, Tongue cancer, Tonsil cancer, Tumors of the adrenal gland, Unknown primary cancer, Uterine cancer, Vaginal cancer, Vulvar cancer, Wilms' tumors, Womb cancer, and Women's cancers (gynecological cancer).

Anticancer Actions. The compositions of the invention attack multiple cancer pathways. A commonality in anticancer pathways may explain why several preclinical studies of each composition of the invention tested show high apoptotic anticancer kill rates over a range of different cancer cell types. Potentially similar pathways are shown by approved metallic anticancer pharmaceuticals like the physicochemical properties of cisplatin and related platinum-based drugs, and they are supported by the evidence collected from their long-term uses (either alone or in combination other drugs) for the treatment of various human cancers. Tchounwou, S. D. (2014 Oct. 5). *Cisplatin in cancer therapy: molecular mechanisms of action.* (S. D. Tchounwou, Ed.) Retrieved 2021 from US National Library of Medicine: https://dx.doi.org/10.1016%2Fj.ejphar.2014.07.025. The metal components of the compositions of the invention are reported, through a significant number of publications on research, and in clinical reports, to have multiple therapeutically beneficial actions on cancer cells. (Krishant M. Deo, 2016). Krishant M. Deo, B. J.-W. (2016 Oct. 31). Transition Metal Intercalators as Anticancer. (S. H. Hadjiliadis, Ed.) *International Journal of Molecular Sciences,* 1-17. Retrieved 2021 from https://doi.org/10.3390/ijms17111818. Mechanisms include reduction of radicals creating oxidative stress, changing metabolic pathways, and opening of cell signaling mechanisms, and these are mechanisms that are exhibited by any one of Zinc, Copper, Manganese, Magnesium, Calcium, Selenium, Potassium, Hydrogen (as $H_3O^+$ in the invention), and SOD, all of which may themselves be incorporated into compositions of the invention. There is a wide range of evidence about the regulatory roles exerted by ion channels and transporters upon the phases of the cell cycle, and other aspects of cell physiology that change or shape multistep neoplastic progression, such as resistance to apoptosis, cell invasiveness, and angiogenesis. Andrea Becchetti, L. M. (2013). The role of ion channels and transporters in cell proliferation and cancer. *Frontiers in Physiology,* 1. https://doi.org/10.3389/fphys.2013.00312. The compositions of the invention are administered for the treatment of cancer in a variety of ways: intravenously (IV), intramuscularly (IM) orally (PO), subcutaneously (SC), intralesionally (IL), intrathecally (IT), and topically. Use of the specific metal ions carried in the compositions of the present invention lowers the toxicity levels seen in current cancer drug treatments. Studies have demonstrated a significant decrease in SOD enzymatic activity in a variety of human cancers. As a result, increased levels of oxidative stress enhance the progression of tumor formation and cancer incidence, but the compositions of the invention antagonize increases in levels of oxidative stress.

Iontophoretic Transport. The compositions of the invention can be used separately or adjunctively combined with chemotherapy or used as a chemosensitizer to treat cancers, cancer tumors, and cancer circulating stem cells. The ionic homeostasis induced following administration may start a cascade of signaling events, ultimately leading to cancer cell death. Studies have implicated the modulation of cellular ion homeostasis by either activation or deactivation of ion transporters and ion channels, which is the mechanism of action of compositions of the invention, in sensitizing cancer cells to otherwise ineffective drugs. Kaushik, V. Y. (2018). Ionophores: Potential Use as Anticancer Drugs and Chemosensitizers. *US National Library of Medicine,* 2. https://dx.doi.org/10.3390%2Fcancers10100360. Current research presents a body of evidence that suggests that an altered ion transport dynamic is present in cancer cells. Cancer cells rewire their cellular circuitry to establish, adopt, proliferate, and metastasize in various challenging conditions by manipulating their ion homeostasis and ion channels, and ion pumps play a critical role in this reorganization.

Treatment of Pathogenic Infections. Another major goal and feature of the invention is the ability to treat pathogenic disease, including compositions that may treat pathogens known as infectious agents, viruses, bacteria, whether gram-negative bacteria or gram-positive bacteria, methicillin-resistant staph aureus (MRSA), fungi, protozoa, parasites, worms, Lyme disease, and biofilm, among others. It is now widely known that a variety of metal ions are toxic to bacteria. Overall, the metals that are being increasingly considered for antimicrobial agents are typically within the transition metals of the d-block (V, Ti, Cr, Co, Ni, Cu, Zn, Tb, W, Ag, Cd, Au, Hg) and a few other metals and metalloids from groups 13-16 of the periodic table (Al, Ga, Ge, As, Se, Sn, Sb, Pt, Te, Pb, and Bi). Of major importance is the discovery made over ten years ago that metals have strong efficacy against microbes growing as a biofilm. Turner, R. J. (2017 Jul. 26). Metal-based antimicrobial strategies. *Microb Biotechnol,* 1062-1065. https://doi.org/10.1111/1751-7915.12785. A quintessential phenotype of biofilms is their ability to confer antimicrobial resistance, and the metals described above actively degrade the ability to construct or maintain such biofilms. Furthermore, such metals have shown some efficacy on those cells that are the dormant variants of normal cells impervious to antibiotics. The biological properties of these compounds can be explained based on several factors including type of donor atom present in ligands, metal ion type, and coordination geometry Pahont, E. (2017, April 19). Synthesis, Characterization, Antimicrobial and Antiproliferative Activity Evaluation of Cu(II), Co(II), Zn(II), Ni(II) and Pt(II) Complexes with Ioniazid-Derived Compound. *International Journal of Molecular Sciences,* 4. From https://dx.doi.org/10.3390%2Fmolecules22040650. Pathogens are known to compete for limited amounts of metals that are necessary to the functionality of the pathogen's metabolism within a host, while simultaneously possessing biological systems that shield themselves from metal toxicity. Pathogens have developed a series of metal regulatory, acquisition, and efflux systems. The compositions of the invention have specific metal ratios to cause disruptions in such pathogen defense systems.

Lower order organisms are not as complex regarding their metabolic pathways as are the higher-order organisms. The cycle followed by lower-order diseases caused by organisms such as bacteria, fungi, and viruses follow a less complicated process that allows the disease to multiply at an almost exponential rate based on available resources in an anaerobic cycle that has far fewer steps. This invention exploits that difference.

Treatment of Autoimmune Disorders. The next major feature and object of the present invention is to provide compositions for the treatment of autoimmune disorders. Autoimmune disorders include Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune Inner Ear Disease (AIED), Autoimmune myocarditis, Autoimmune oophoritis, Autoimmune orchitis, Autoimmune pancreatitis, Autoimmune retinopathy, Autoimmune urticaria, Acute Motor Axonal Neuropathy (AMAN), Baló disease, Behcet's disease, Benign mucosal pemphigoid, Bullous pemphigoid, Castleman Disease (CD), Celiac disease, Chagas disease, Chronic Inflammatory Demyelinating Polyneuropathy (CIDP), Chronic Recurrent Multifocal Osteomyelitis (CRMO), Churg-Strauss Syndrome (CSS), Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic Esophagitis (EoE), Eosinophilic fasciitis, Erythema nodosum, Essential mixed cryoglobulinemia, Evans syndrome, Eczema, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein Purpura (HSP), Herpes gestationis or Pemphigoid Gestationis (PG), Hidradenitis Suppurativa (HS), Acne Inversa, Hypogammaglobulinemia, IgA Nephropathy, IgG4-related sclerosing disease, Immune Thrombocytopenic Purpura (ITP), Inclusion Body Myositis (IBM), Interstitial cystitis (IC), Juvenile arthritis, Juvenile diabetes (Type 1 diabetes), Juvenile Myositis (JM), Kawasaki disease, Lambert-Eaton syndrome, Leukocytoclastic vasculitis, Lichen planus, Lichen sclerosis, Ligneous conjunctivitis, Linear IgA Disease (LAD), Lupus, Chronic Lyme disease, Meniere's disease, Microscopic polyangiitis (MPA), Mixed Connective Tissue Disease (MCTD), Mooren's ulcer, Mucha-Habermann disease, Multifocal Motor Neuropathy (MMN), MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis Palindromic Rheumatism (PR) PANDAS, Paraneoplastic Cerebellar Degeneration (PCD), Paroxysmal Nocturnal Hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious Anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure Red Cell Aplasia (PRCA), Pyoderma gangrenosum, Raynaud's phenomenon, Reactive Arthritis, Reflex sympathetic dystrophy, Relapsing polychondritis, Restless Legs Syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff Person Syndrome (SPS), Subacute Bacterial Endocarditis (SBE), Susac's syndrome, Sympathetic Ophthalmia (SO), Takayasu's arteritis, Temporal arteritis/Giant cell arteritis, Thrombocytopenic Purpura (TTP), Thyroid Eye Disease (TED), Tolosa-Hunt Syndrome (THS), Transverse myelitis, Type 1 diabetes, Ulcerative Colitis (UC), Undifferentiated Connective Tissue Disease (UCTD), Uveitis, Vasculitis, Vitiligo, and Vogt-Koyanagi-Harada Disease.

Autoimmune diseases represent the phenomenon of a body's own immune cells attacking the host's own cells and tissue. Five to eight percent of the world's population are currently affected by 80-100 autoimmune diseases. The compositions of the present invention bring several known and several potential mechanisms of action, in combination, to address the treatment of autoimmune disease by changing the conditions of the radical SOD1 enzyme, by pathogenic involvement, and by reducing an over-simplified immune system through treating the underlying problem. The antioxidant properties of the compositions of the invention that have high ORAC and ORP values provide additional rational approaches to the reduction of immune responses, thereby potentially relieving or reducing Autoimmune diseases.

Zinc, in the form of the zinc cation, is a component in many of the preferred embodiments of the invention and is recognized as constituting a targeted approach to autoimmune disorders. Its homeostasis behavior is essential against inflammatory diseases to regulate the immune system's different aspects, both for innate and for adaptive immune response, cell cycle progression, and cell maturation and differentiation. Zinc deficiency is therefore associated with the incorrect maturation and function of T and B cells, an unbalanced ratio between Th1 cells and Th2 cells, and between regulatory and pro-inflammatory T cells, as well as a weakening of NK cell function. Alessandro Sanna, D. F. (2018 Jan. 11). Zinc Status and Autoimmunity: A Systematic Review and Meta-Analysis. (Nutrients, Ed.) *Nutrients,* 10(1), 68. From https://dx.doi.org/10.3390%2Fnu10010068.

Copper is a preferred component in the compositions of the invention. Patients suffering from inflammatory rheumatic diseases were found to be almost totally depleted of the low-molecular-weight copper protein copper thionein, which exerts pronounced superoxide dismutase activity and scavenges hydroxyl radicals and singlet oxygen effectively. Ralf Miesel, M. Z. (1993, June). Copper-dependent antioxidase defenses in inflammatory and autoimmune rheumatic diseases. *Inflammation,* 283-294. From https://doi.org/10.1007/BF00918991.

Hydrogen, present as a hydronium ion, is a preferred component of the compositions. It is an object of the invention to reduce levels of reactive oxygen species (ROS), particularly the ·OH hydroxyl radicals, which are thought to be critical drivers of the type of tissue damage that occurs in many autoimmune diseases, particularly Psoriasis and Rheumatoid Arthritis. Decker, C. (2019 Nov. 12). *Harnessing Hydrogen's Antioxidant Power to Treat Autoimmune Disease.* From Holistic Primary Care: https://holisticprimarycare.net/topics/chronic-disease/harnessing-hydrogen-s-antioxidant-power-to-treat-autoimmune-disease/.

Homeostasis in RSS, RNS, and ROS. Yet another feature and object of the invention is to achieve and maintain redox balance and biological homeostasis in the presence of reactive oxidative species, namely reactive oxygen species, ROS, reactive nitrogen species, RNS, and reactive sulfur species, RSS. When an overload of free radicals cannot timely be destroyed, their accumulation in the body generates a phenomenon called oxidative stress. Oxidative Stress has been clinically proven to be involved in hundreds of diseases. Compositions of the invention may reduce and balance free radicals such as, and not limited to, reactive oxygen species, reactive nitrogen species, and reactive sulfur species, each of which cause oxidative damage and cellular dysfunction.

Mitochondrial Support. The compositions of the invention transport molecular signals activating stress responses within the mitochondria that are beneficial to the biological system. Transport pathways play a significant role in the reduction of tissue oxidative damage and dysfunction. The compositions protect against excessive tissue dysfunction through several mechanisms, including stimulation of opening of permeability transition pores.

Additional goals, features, and advantages of the invention as disclosed and claimed herein include the following non-limiting list within certain uses and fields, these uses made possible by the biological properties of the compositions of the invention.

Pharmaceutical Oral and Topical Treatments. Uses of the compounds of the invention in topical treatment can be used to treat infections, effectuate load-reduction of pathogens, and as an adjunct or replacement for antibiotics; to create high kill-rates for the treatment of all viruses, fungi, methicillin resistant staph aureus (MRSA), Gram-Negative or Gram-Positive bacterial infections, and parasitic infections; to reduce average treatment times and reduce prolonged symptoms in the treatment of viruses, fungi, MRSA, Gram-Negative and Gram-Positive Bacterias and Parasites; and infectious and systemic diseases, including, but not limited to, Alzheimer's disease, Lyme disease, MRSA, or any other pathogenic-related disease.

Passage through and reduction of biological biofilm. The synthesized ionophores of the invention are able to pass through and reduce biofilm (extracellular polymeric substances) to mimic or create antipathogenic toxicity of cellular RNA replication, thereby acting to reduce viral, fungal, and bacterial loads on the system, or to reduce antibiotic resistance within these pathogens.

Use as an antioxidant in inflammation reduction. Due to their antioxidant properties, the compositions of the invention are useful in pain management therapies, and anti-inflammatory therapies. The compositions are non-ototoxic, unlike many anti-inflammatories, both steroidal and non-steroidal.

Skin trauma. The compositions can be used on damage to the skin or other areas exposed to external factors, including damage caused by excess exposure to sunlight, extreme heat, flame, contact with hot objects, radioactive burns, or chemical burns, and used in providing burn pain relief.

Wound healing. Increases in the rate of wound healing, as well as in pre-traumatic, and post-traumatic, or pre-surgery or post-surgery intervention, can be achieved with compositions of the invention.

Vascular Disorders. Vascular disorders, including heart disease, arteriosclerosis, thrombosis, and cardiovascular disorders can be addressed using compositions of the invention.

Additional indications. The compositions of the invention may also be useful: as a smooth muscle relaxant, encompassing a broad spectrum of agents that relax both vascular and nonvascular smooth muscle disorders; as part of the treatment of all cancer cell types, including reducing cancer solid tumors and non-solid cancers, cancers of the circulating stem cells, cancers in the metastasis phase, and pre-cancerous atypical cells, treatment of all skin cancer cell types while additionally providing positive eschar actions, as an adjunct with pre-surgical and post-surgical cancerous and pre-cancerous cell removal procedures, as an adjunct in Mohs surgery, and as an adjunct or replacement for chemotherapy creams; in auto-immune disorders, including, but not limited to, psoriasis and eczema; neurological disorders, migraine headache of neurological origin, cardiovascular stroke recovery, Multiple Sclerosis, traumatic nerve injury to nerves of the peripheral nervous system and the central nervous system, Amyotrophic Lateral Sclerosis, Alzheimer's disease, epilepsies, and epileptic seizures, and smooth and striated muscle relaxation; arthritis and arthritic conditions due to their role in the reduction of oxidative stress and levels of free radicals in a region afflicted by over-production of a superoxide detoxification of a biological system, especially an avian system, a mammalian system, or a human system, for preventative or medicinal clearing of toxic substances therefrom; in nasal administration as a spray or drops for sinus congestion, sinus cleansing, or for sinus infections; reduction of Alzheimer's and non-Alzheimer's dementia, and for the improvement of cognitive enhancement; for use in psychiatric disorders, including schizophrenia, depression, and Post Traumatic Stress Disorder (PTSD), as well as other severe mental disorders and complicated diagnostic stress issues in a patient; or as a formulation delivering the compositions of the invention, solely or in combination with other carrier formulations.

The compositions may further be used as: a pharmaceutically acceptable oral, otic. ophthalmic, buccal, sinus, vaginal, urethral, rectal or topical medication; an image enhancing agent in PET or CT scans, and as a preliminary contrast media; an antimicrobial applied as a therapeutic mist or spray over an infected area; agents causing the reduction of free radicals and cells mutated by radiation exposure or from overdosing radiotherapy treatments or radio imaging; agents to reduce infection from implants or prosthetic device surgeries; infection reduction agents from Intravenous therapy, injections, catheters, implanted access ports, or other invasive medical devices; dentistry applications and uses, including dental infections and treatments of a tooth's root; cavities (caries) prevention and treatment of the teeth; and infection prevention and treatment of the teeth or gums, gingivitis prevention and treatment, or improved dental hygiene outcomes, all in a paste, gel, gum, spray, chewable tablet, buccal tablet, or injectable formulation.

The compositions of the inventions are also useful for: fixed dose combination or monotherapy formulations compounded to achieve a specific drug indication and systemic delivery profile in fixed dose combinations with oncology drugs and their delivery formulations, narcotic drugs and their delivery systems, in combination with protein enhancement or protein synthesis blockading therapies; in combination with hormone enhancement or blocking therapies in the treatment of endocrinological disorders; in combination with cellular receptor-blocking or cell signaling modification therapies; in combination with biological or biosimilar products that are relatively large, complex molecules that may be produced through biotechnology in a living system, including microorganisms, plant cells, or animal cells; combined biological actions that provide anticancer cell death through apoptosis, antipathogenic cell death through necrosis, and change within a diseased environment to regress or stabilize anaerobic cell growth; in coordinated usage with redox biology and redox medicine strategies to obtain therapeutic benefits and treatments that affect an outcome by modifying the levels of pro-oxidant and antioxidant agents in cells; in personal care and cosmetic skin care products; in cosmetic formulations for medical and non-medical skincare products; in skin antiaging, repair, esthetic beautification, moisturization, and skin restoration, in tanning acceleration, in sunscreens, in treatment of sunburns and in reduction of free radical generation occurring as a result of exposure to sun; a nontoxic preservative and antimicrobial excipient in formulations.

Penetration and absorption of a substance into skin, membranes, tissues, and organs is affected by the physicochemical properties of pharmaceutical formulations compounded for such delivery purposes, and the compositions of the present invention enhance and support such skin penetration and absorption.

The compositions of the invention are characterized by a low pH, by high redox values (positive electrical charge), and by the inherent powers of natural metal cations and water to coordinate together and then to react with oxidative reactive species, nitrogen reactive species, and sulfur reactive species, to result in a novel cellular delivery method.

The invention utilizes preferred compounds within a composition that is a formulation of aqueous ligands in a hexa-aqua delivery system. A preferable active compound is a synthesized ionophore that actively transports free ions to the shells of cell membranes or through cell membranes to interact with internal/external cellular environments. The metal ionic structures in the aqueous solution are primarily in a hexa-aqua octahedral ligand configuration. The metal ionic structures are alternatively in a tetra-aqua tetrahedral or planar geometry. These lower-order ionic structures may configure to higher-order complex ionic structures based on anionic and cationic equilibriums which contain a high level of free sulfur, amines, sulfate ions, metal hexa-aqua structures, metal hydroxyl/aqua mixed ligand species, and H+. These ionic structures utilize amine and sulfate ions in concert with free protons (H+) in specific ratios to enable effective bridging of multiple metal-aqua species nearby, creating a concentrated ionophoric metal ion delivery system through cellular membranes.

The equilibrium between these ionic metal structures and stabilized free anions and cations in solution is crucial to the stability and steric proximity of the coordinating metal ions in order to provide effective cell wall penetration and delivery of the metal ions to a host of intracellular biological processes to address the metabolic and pathological conditions described above. By modifying the concentrations of the ionic compounds and H+ in aqueous solution, the system of the present invention can be fine-tuned to penetrate and deliver metal ions into a multitude of cell types, to attach to cellular walls, or to provide a pathway for single metal ions or complex metal ionic bridged structure delivery. The composition compounds of the present invention enter cells and deliver one or more structures therein to impact biological processes and mechanisms in humans or animals.

A complex ion has a metal ion at its center with several other molecules or ions, creating inorganic coordination complexes or coordinate (dative covalent) bonds where both electrons come from the same atom. A covalent bond forms by two atoms sharing a pair of electrons. The atoms hold together because both nuclei attract the electron pair. The invention has created a unique relationship with ligand bonding, becoming the carrier or co-bonding mechanism with other molecules to move within biological systems. The anions or molecules attached to the metal are the ligands. The coordination number is the number of places on the metal ion where ligands are bound. The bond between the metal ion and the ligand, where the ligand supplies both electrons, is a coordinate covalent bond. Simple ligands include water, ammonia, phosphorus, and chloride ions.

Every metal ion has at least one coordination sphere, which determines the number of coordinate bonds possible for each metal atom. The coordinate bonds attract negatively charged ions possessing unshared electron pairs. The cations use the unshared pair to fill gaps in the outer electron orbitals where those electron shells are incomplete. All the 3-level orbitals are now empty, making use of all six empty orbitals to accept lone pairs from six water molecules. The moiety re-organizes (hybridizes) the 3s, the three 3p, and two of the 3d-shell orbitals to utilize six orbitals, all with similar energy. Six is the maximum number of water molecules around most metal ions, comprising the maximum number of bonds, and is the most energetically stable. The bonds formed between the cations and the unshared pairs of electrons become hexa-aqua ligand bonds.

The most preferred embodiments of the present invention will use each of six water molecules as a hexa-aqua ligand attached to a central metal cation via a coordinate bond using one of the available lone pairs on oxygen. These metal hexa-aqua species then form higher-order ionic structures with the amine and sulfate ions in concert with H, which is effectively bridging multiple metal aqua species nearby, creating an iontophoretic metal delivery system. The equilibrium between these ionic metal structures and stabilizing free anions and cations in solution is crucial to the stability and steric proximity of the coordinating metal ions to provide effective cell wall penetration and delivery of the metal ions to a host of intracellular biological processes. By modifying the concentrations of the ionic compounds and free hydrogen in the solution, the ionophore delivery system of the invention can be custom synthesized and formulated to penetrate and deliver metal ions into cells, attach to cellular walls, and provide a pathway for single metal ions or complex metal ionic bridged structures. A preferred embodiment composition is illustrated in FIG. 5, to show a delivery system formulation in which six water molecules are present, that may form hexa-aqua ligands with any metal cations of $Zn^{2+}$, $Cu^{2+}$, or $Mg^{2+}$, here forming hexa-aqua copper, hexa-aqua zinc, and hexa-aqua magnesium species, in the presence of $NH_4^+$, $H^+$, and $HSO_4^-$ ions, in a pharmaceutical formulation soup-like milieu of cationic ligands and ionic salts.

Ionophore delivery. Ionophores are any of a number of naturally occurring carrier of ions. The present invention is a synthesized ionophore that can mimic natural versions of ionophores or create similar ionophore signaling functions to produce enzymes, protein actions, and electron transfers in biological systems' metabolic processes. The compounds of the present invention that comprise the therapeutic compositions have multiple ionophore pathways available to them through cellular membranes. Thus, they allow entry through all tissue, blood, organ, and cellular barrier types. Ion channels are membrane proteins found in all domains of cellular life. They are present in all intracellular membranes as well as the plasma membrane. Transport mechanisms through these ion channels allows for the compounds of the invention to have multifunctional forms of permeability.

Fluid and ion transfer across the blood-brain and blood-cerebrospinal barriers are highly restrictive due to tight junctions creating a fluid barrier. Hladky, S. B. (2016). Fluid and ion transfer across the blood-brain and blood-cerebrospinal fluid barriers; a comparative account of mechanisms and roles. (S. Nature, Ed.) *Springer Nature,* 1. Retrieved from https://doi.org/10.1186/s12987-016-0040-3. Since the compounds of the present invention are preferably an ionophore of water, their ligand structure, and low pH, allows for higher permeability across these tight central nervous system transport junctions. This provides for a higher ion delivery rate than most current methods of drug delivery. Filip Vlahovic, M. P. (2015, June 7). Assessment of TD-DFT and LF-DFT for study of d-D transitions in first row transition metal hexaaqua complexes. *Researchgate,* 142, 214111. Retrieved 2021 from https://www.researchgate.net/figure/The-structure-of-investigated-hexaaqua-transition-metal-ion-complexes-MH-2-O-6-n_fig4_277895193.

Passive Transport. As a hexa-aqua water-based carrier, a preferred compound of the present invention will have simple concentration gradients. Water is found in different concentrations over a region of cellular space or on opposite sides of a membrane; therefore, water is highly neutral and absorbent in biological systems and allows the compounds utilized in the present invention to engage in a very passive degree of transport. Large quantities of water molecules continuously move across cell membranes by osmosis, a simple diffusion process through membrane proteins and aquaporins movement. Lumen. (2020). *Membrane Transport.* (Pressbooks, Editor, & Pressbooks) From The Cellular Level of Organization: https://courses.lumenlearning.com/nemcc-ap/chapter/3204/ Up to one hundred times the volume of a cells water molecules will diffuse across, e.g., a red blood cells membrane every second; the cell does not lose or gain water because equal amounts go in and out through osmosis, the effect of which is to make the hexa-aqua ligand an extremely efficient delivery system. The hexa-aqua ligands found in the present invention take advantage of osmosis, tonicity, and hydrostatic pressure in a passive transport system in which water flows from the membrane with the lower solute concentration into the membrane with higher solute concentration. The hexa-aqua ligands of the invention carry a free ion with low molecular weight, allowing for passive entry, and potentially can deliver larger molecules that are hidden in a biological soup comprised of ionophore carriers and their respective bonded molecules.

Active transport. The synthetic ionophore compounds of the invention have a highly positive electron charge providing an electrical gradient, or difference in charge, across a plasma membrane, an atypical condition found in biological active transport. Living cells typically have a membrane potential, which is an electrical potential difference (voltage) across their cell membrane. Electrical potential differences exist whenever there is a net separation of charges in that space. In the case of a cell, positive and negative charges are separated by the cell membrane's barrier, with the inside of the cell having extra negative charges relative to the outside.

Sodium and Potassium Pathways. The compositions of the invention exploit the actions of sodium and potassium pathways. The inside of a cell has a higher concentration of potassium and a lower sodium concentration than the extracellular fluid around it. When sodium ions are outside of a cell, they will tend to move into the cell based on their concentration gradient and the voltage across the membrane (the more negative charge on the inside of the membrane). The combination of the concentration gradient and voltage that affects an ion's movement is the electrochemical gradient that is a property of the compounds of the invention.

Primary and Secondary Active Transport. The ionophore compounds of the invention can be designed to affect different transports in the case of a primary transport known to use ATP as a source of energy. Presence of a magnesium ion is required for this energy production. In the case of a secondary active transport (cotransport), the ionophores of the invention use an electrochemical gradient cationic charge as an attractant to move molecules against their gradient and thus does not directly require a chemical source of energy such as ATP. Through variation of stoichiometry ratios of ions, the compounds of the invention can be designed to target the desired transfer method.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss or diminution of generality to, and without imposing limitations upon, the claimed invention.

As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art on how to make or use the embodiments of the disclosure and are not intended to limit the scope of the disclosure of the invention, which is defined solely by the claims.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Minerals are naturally occurring chemical compounds comprising metal elements, and they are often required as essential nutrients by organisms to perform functions necessary for life. Metals have played an essential role in biological systems from the beginning of time. As catalytic or structural cofactors, metal ions are critical to the function of as many as one-third of all enzymes by some estimates, and they have extensive roles in biological systems.

An ionophore is a chemical species that reversibly binds ions. Many ionophores are lipid-soluble entities that transport ions across the cell membrane. Ionophores catalyze ion transport across hydrophobic membranes, such as liquid polymeric membranes (carrier-based ion selective electrodes) or lipid bilayers found in the living cells or synthetic vesicles, for example liposomes. Structurally, an ionophore contains a hydrophilic center and a hydrophobic portion that interacts with the membrane. Some ionophores are synthesized by microorganisms to import ions into their cells. The compositions of the invention comprise compounds that are synthetic ionophores. Ionophores selective for cations and anions have found many applications in analysis. These compounds have also been shown to have various biological effects and a synergistic effect when combined with the ion they bind.

Biological activities of metal ion-binding compounds can be changed in response to the increment of the metal concentration, and based on the latter characteristic, compounds can be classified as "metal ionophores", "metal chelators" or "metal shuttles". If the biological effect is augmented by increasing the metal concentration, it is classified as a "metal ionophore". If the biological effect is decreased or reversed by increasing the metal concentration, it is classified as a "metal chelator". If the biological effect is not affected by increasing the metal concentration, and the compound-metal complex enters the cell, it is classified as a "metal shuttle".

The term p-block element means an element from the group consisting of Phosphorus (P), Boron (B), Nitrogen (N), Carbon (C), Sulfur (S), Oxygen (O), Aluminum (Al), Fluorine (F), Bromine (Br), Indium (In), Silicon (Si), Arsenic (As), Argon (Ar), Lead (Pb), Bismuth (Bi), Chlorine (Cl), Tin (Sn), Iodine (I), Neon (Ne), Selenium (Se), Germanium (Ge), Xenon (Xe), Antimony (Sb), Tellurium (T), Krypton (Kr), Polonium (Po) Nihonium (Nh), Radon (Rn), Moscovium (Mc), Oganesson (Og), Flerovium (Fl), Livermorium (Lv), and Tennessine (Ts).

The term d-block element means an element from the group consisting of Zinc (Zn), Copper (Cu), Chromium (Cr), Iron (Fe), Nickel (Ni), Cobalt (Co), Mercury (Hg), Gold (Au), Manganese (Mn), Cadmium (Cd), Silver (Ag), Titanium (Ti), Vanadium (V), Yttrium (Y), Ruthenium (Ru), Palladium (Pd), Molybdenum (Mo), Tungsten (W), Hafnium (Hf), Niobium (Nb), Zirconium (Zr), Osmium (Os), Platinum (Pt), Rhodium (Rh), Technetium (Tc), Tantalum (Ta), Bohrium (Bh), Copernicium (Cn), Lutetium (Lu), Rutherfordium (Rf), Roentgenium (Rg), Lawrencium (Lr), Meitnerium (Mt), Hassium (Hs), Darmstadtium (Ds), Dubnium (Db), and Seaborgium (Sg).

The term s-block element means an element from the group consisting of Potassium (K), Hydrogen (H), Beryllium (Be), Sodium (Na), Magnesium (Mg), Lithium, (Li), Calcium (Ca), Barium (Ba), Caesium (Cs), Rubidium (Rb), Strontium (Sr), Francium (Fr), Radium (Ra), and Helium (He).

Abbreviations, nomenclature, and technical & non-technical term definitions as used in these Examples are as follows:

The phrase "A" or "an" in the context of an entity or moiety as used herein refers to one or more of that entity or moiety, as in for example, "a" compound refers to one or more compounds or at least one compound. As such, the terms "a" (or "an"), "one or more," and "at least one," and "and or "can" be used interchangeably. The term "about" has its plain and ordinary meaning of "approximately." Regarding metal ion ratios and dosing amounts, the qualifier "about" reflects the standard experimental error. The terms "optional" or "optionally" as used herein means that a subsequently described event or circumstance may, but need not, occur and that the description includes instances where the event or circumstance occurs and instances in which it does not. The term "subject" as used herein, means any species in need of therapy or supplementation, both non-mammalian and mammalian animals, and humans. Preferably the subject is a human. The term "preparation" and "compound" or "compounds" and "formulation" or "formulations" is intended to include any of solid, liquid, or gaseous formulations of the active compounds, and one skilled in the art will appreciate that an active pharmaceutical ingredient ("API") can exist in different preparations depending on the desired dose and pharmacokinetic design parameters. The terms "compositions" and "excipient" and "pharmaceutical excipient" as used herein refer to a compound used to prepare a pharmaceutical composition and is generally safe, non-toxic, and neither biologically nor otherwise undesirable, and includes excipients that are acceptable for veterinary use as well as human pharmaceutical use. The term "dosage" intends to include either or both solid and liquid formulations of the active compound, and one skilled in the art will appreciate that an active ingredient can exist in different preparations of administration methods, percent of the API, prescribed dose, length of use, time of use, type of indication, desired outcome, and pharmacokinetic design parameters. The term "mixing" or "efficient mixing" as used herein is not limited to the same compounding process; it involves all mixing methods in a manufacturing process. The term "biological system", as used herein, refers to the interactions of the key elements such as DNA, RNA, proteins, and cells concerning one another in a subject. The term "Iontophoresis," as used herein, is a process of transdermal drug delivery by use of a voltage gradient for electromotive drug administration (EMDA) on the skin. Molecules are transported across the stratum corneum by electrophoresis and electroosmosis, and the electric field can also increase the permeability through tissue membranes for diagnostic or therapeutic use. As used herein, "treatment" or "treating" or "therapy" or "therapeutic" or "medicaments" or "prevention" is an approach for obtaining beneficial or desired clinical results. Beneficial or desired clinical results include, but are not limited to, prevention, alleviation of symptoms, diminishment of the extent of disease, stabilized state of disease, delay or slowing of disease progression, amelioration or palliation of the disease state, and remission, whether detectable or undetectable in part or total. "Treatment" can also mean prolonging survival as compared to expected survival if not receiving treatment. "Treatment" is an intervention performed to eliminate or prevent a disease or develop to eliminate or prevent a disease or alter a medical disorder's pathology in a biological system. The term "Ion Biotechnology® Hexa-aqua Delivery System", describes the invention as being a combination of Ion Biotechnology® Aqueous Ligands, which will be abbreviated as "IBAL".

"API"=Active Pharmaceutical Ingredient.

"Acid Mix"=A preparatory mixture of acids for use in the production of compositions of the invention, to receive metal salts or combinations thereof, as disclosed below.

API=Active Pharmaceutical Ingredient

BP=British Pharmacopoeia

CAS=Chemical Abstract Service Registry Number

EP=European Pharmacopoeia

FEUM=Farmacopea de los Estados Unidos Mexicanos

Ionophore=A substance which may reversibly bind ions and to transport reversibly bound ions across a lipid membrane in a cell.

NF=National Formulary

ORAC=Oxygen Radical Absorbance Capacity

ORP=Oxidation Reduction Potential

USP=United States Pharmacopoeia

Exogenous nutrient elements modulate the energetic metabolism responses that are prerequisites for cellular homeostasis and metabolic physiology. Specifically, the delivery of micronutrients in the form of metals is critical in oxidative stress and cytoprotecting processes. Commonly administered minerals and drugs are not in a highly bioavailable form nor can they target the immediate area of therapeutic or nutritional need. They are commonly unable to effectively or efficiently cross through a hydrophobic lipid bilayer membrane, whether by active transport, or by passive transport, and often for this reason fail to activate a natural therapeutic response. With nutrients, a key factor in membrane transport is the solubility of nutrients as determined by their molecular polarity properties (Dewey Holten, 1999).

Small molecule drugs widely disburse, and the more pharmacologically promiscuous they are, the more cell types are targeted, exacerbating the appearance of multiple side effects, while many may not be able to travel to the cell adequately or at all to exert their pharmacologic action or correctly or adequately influence extracellular pathways. The present invention, or Ion Biotechnology® Aqua Ligand (IBAL), provides an effective carrier of polarized molecules via active transport across cell membranes. Natural active transport also occurs, as the osmotic pressure of water created by the presence of hexa-aqua ligands creates a dispersion of free ions facilitated by polarity and size (small molecular weight) throughout the interstitial fluids, increasing direct uptake through the lipid bilayer of the cellular membrane and into the cytoplasm of the cell.

Reactions of the preferred embodiment hexa-aqua complexes of the invention in an ammonia solution are complex because ammonia can act with two significantly different functions. Firstly, ammonia can act as a Bronsted-Lowry base, a ligand, or as a Lewis Base (Clark, J., Reactions of the Hexa-aqua Metal Ions With an Ammonia Solution, (2017, April 1), (Chemguide, Editor) Retrieved 2021 from Chemguide: https://www.chemguide.co.uk/inorganic/complexions/aquanh3.html#top. Secondly, ammonia is also a possible ligand that can bond with water molecules around a central metal ion. This ligand appears when small amounts of a dilute ammonia solution is added to metals, creating a hexa-aqua ligand solution or a mixed aqua amine ligand system. At equilibrium, amines are acting as acids by donating hydrogen ions to water molecules in the solution. According to Le Chatelier's Principle (When any system at equilibrium for a long period of time is subjected to a change in concentration, temperature, volume, or pressure, the system changes to a new equilibrium, and this change partly counteracts the applied change), if the ligand solution is increasing in pH, the equilibrium position will move to production of more of the new ammonia complex ions replacing hydronium ions A unique property of the present invention is the coordinated complex ionic structure that maintains the solution's equilibrium by two reactive processes. An ammonia molecule is more likely to cause the replacement of a water ion on the metal, instead of the reverse exchange reaction that occurs when the pH is low (under 1.0). If that low pH reaction is allowed to go too far, it will create a "neutral complex" consisting of one or more hydroxyl groups or mixed hydroxyl ($OH^-$), water, and or amine groups, which can be insoluble in water, and so a precipitate is formed. When ammonia is acting in a ligand exchange reaction, ammonia replaces water around the metal ion to give a soluble complex. There is thus an interaction between the two equilibria. To obtain a dissolved precipitate, the invention needs the ligand exchange equilibrium to be correct to maintain ionic stability, but the invention also needs for the acid-base equilibrium to be easily manipulated in reverse as well. The present invention solves the difficulty in obtaining this required balance in the reaction process. The present invention, including its most preferred embodiment, an Ion Biotechnology® Aqueous Ligand (IBAL) has been manufactured and researched in these completed complexes including obtaining the pH levels, Redox Potential values (ORP), and metal cation ratios described herein for the invention. Multiple in-vitro, in-vivo, and preclinical animal and human trials have been performed, supporting the invention's safety, components, efficacy, and modes of action in biological systems.

The number of ammonia molecules is double the metallic ion valence, and the valence charge does not change at a low pH. The unshared pair of electrons from the ligand bond is the ligand system supplying both the unshared electrons to a free hydrated metal ion. The use of transition metals is critical to obtain the proper ligand bond. Transition Metal Ions may act as Bronsted Acids while others like $Cu^{2+}$ cannot by themselves, due to the delocalization of charge to one or more of the aqua ligands becoming acidic. The hydration reaction is defined as the transfer of an ion or a neutral chemical species from the gaseous phase into water; for metal ions $Mn^+$ (g)→$Mn^+$ (aq) (Persson, 2010). These ligand reactions give rise to a net increase in the H+ ion concentration in these solutions, thereby making the solutions acidic and a stable ligand exchange equilibrium. To obtain the ligand bond, at least one or more of the elements of the 3d block (scandium to zinc) as a transition metal are preferably and advantageously used in the IBAL coordinated ionic bond complex. See Brown, D. P. (2015). *Introduction to 3d-block Transition Metal chemistry concepts definition data table characteristics variable ions oxidation states colored compounds complexes catalysts high melting points high density*. Retrieved 2021 from Doc Brown's Chemistry: http://www.docbrown.info/page07/transition1.htm.

The addition of metals singly or in combinations of ratios in the manufacturing process include but are not limited to any one of Calcium, Chromium, Cobalt, Copper, Iodine, Iron, Magnesium, Manganese, Molybdenum, Nickel, Potassium, Selenium, Silver, Vanadium, and Zinc and any combination thereof, in any stable oxidation state. Additional compounds are organic or inorganic, such as, but not limited to, chemicals, molecules, proteins, urea, and combinations with other known pharmaceuticals, carriers, and personal care formulations described in the specification and in the claims for method of use.

The compounds of the present invention can be prepared readily according to the following Examples or modifications thereof using readily available starting materials, reagents and conventional synthesis procedures. In these reactions, it is also possible to make use of variants which are themselves known to those of ordinary skill in this art, but these are not mentioned in greater detail.

The most preferred compounds of the invention are any or all of those specifically set forth in these Examples. These compounds are not, however, to be construed as forming the only genus that is considered as the invention, and any combination of the compounds or their moieties may itself form a genus. The following examples further illustrate details for the preparation and the quantitative and qualitative analysis of the compounds of the present invention. Those skilled in the art will readily understand that known variations of the conditions and processes of the following preparative procedures can be used to prepare these compounds.

All temperatures are degrees Celsius unless noted otherwise.

Example 1

A Zinc Hexa-aqua, Copper-Hexa-aqua, Magnesium Hexa-aqua Composition 0.5 Kg Batch: ZCM-5/2/2

| Ingredient | Target Metal ion mass % | Batch mass (Kg) | Mass Percentage |
|---|---|---|---|
| Sulfuric Acid | | 0.0170 | 3.40% |
| Ammonium Sulfate | | 0.0022 | 0.44% |
| Deionized Water | | 0.2301 | 46.03% |
| Zinc Sulfate Heptahydrate | 5% | 0.1100 | 21.99% |
| Cupric Sulfate Pentahydrate | 2% | 0.0393 | 7.86% |
| Magnesium Sulfate Heptahydrate | 2% | 0.1014 | 20.28% |
| Total | — | 0.5000 | 100.00% |

In Step 1, Sulfuric acid was placed into a glass or glass lined reactor and stirred at room temperature. Ammonium sulfate was added while stirring and completely dissolved. Deionized water was then added, drop wise, slowly under constant stirring to minimize the exothermic reaction increasing temperature of the solution above 50 degrees Celsius and maintain a temperature of less than or equal to 45 degrees Celsius. The mixture was mixed to homogeneity and allowed to cool back to room temperature (~25 degrees Celsius).

In Step 2, the zinc sulfate heptahydrate was combined into the solution prepared in Step 1 and mixed until completely dissolved and the solution was homogeneous. Then the cupric sulfate pentahydrate was added and mixed until completely dissolved and the solution was homogeneous. Finally, the magnesium sulfate heptahydrate was then added and mixed until completely dissolved and the solution was homogeneous. Mixing was continued for 12 hours until an even consistency was obtained at room temperature.

Starting material considerations and alternatives: Starting materials to produce $NH_3$ or $NH_4^+$ in an aqueous solution are advantageously ammonium water (0.5-28%), ammonium sulfate or ammonium hydrogen sulfate and sulfamic acid by any method of manufacture known to those of ordinary skill in the art. Starting materials to produce $HSO_4^+$ in an aqueous solution are sulfuric acid (1.0-98% concentration) or sulfamic acid, prepared by any method known to those of ordinary skill in the art. Starting materials to produce any or all of the starting materials to produce metal hexa-aqua ions in an aqueous solution are any metal sulfate, metal nitrate, metal hydroxide, metal hydroxide/amine species, metal amine, metal chloride, metal iodide, metal bromide, metal carbonate, or metal carbonyl including, but not limited to, any combination of ligands stated.

Zinc Hexa-Aqua, Copper-Hexa-Aqua, Magnesium Hexa-Aqua Compositions

Using the procedure of Example 1, the following ingredients in the following w/w % ranges of component ions are combined, depending on administration and application:

| Material | w/w % Minimum | w/w % Maximum |
|---|---|---|
| Sulfuric Acid | 1.00% | 4.50% |
| Ammonium Sulfate | 0.01% | 5.00% |
| Deionized Water | 35.00% | 75.00% |
| Zinc Sulfate Heptahydrate | 10.00% | 30.00% |
| Cupric Sulfate Pentahydrate | 5.00% | 10.00% |
| Magnesium Sulfate Heptahydrate | 10.00% | 30.00% |

Example 2

Zinc Hexa-aqua, Copper-Hexa-aqua, Magnesium Hexa-aqua and Selenous acid Composition:
ZCMS-5/2/1/1 in a 0.5 Kg batch

| Ingredient | Target metal ion mass percentage: | Ingredient mass (Kg) | Mass percentage (w/w %) |
|---|---|---|---|
| Sulfuric Acid | — | 0.01997 | 3.99% |
| Ammonium Sulfate | — | 0.00259 | 0.52% |
| Deionized Water Type 1 | — | 0.27049 | 54.10% |
| Zinc Sulfate Heptahydrate | 5.0% | 0.10992 | 21.98% |
| Cupric Sulfate Pentahydrate | 2.0% | 0.03929 | 7.86% |
| Magnesium Sulfate Heptahydrate | 1.0% | 0.05070 | 10.14% |
| Selenium Dioxide | 1.0% | 0.00704 | 1.41% |
| Total | — | 0.5 | 100% |

In Step 1, Sulfuric acid was placed into a glass or glass lined reactor and stirred at room temperature. Ammonium sulfate was added while stirring until completely dissolved. Deionized water was then added, drop wise, slowly under constant stirring to minimize the exothermic reaction increasing temperature of the solution above 50 degrees Celsius and maintain a temperature of less than or equal to 45 degrees Celsius. The mixture was mixed to homogeneity and allowed to cool back to room temperature (~25 degrees Celsius).

In Step 2, the zinc sulfate heptahydrate was combined into the solution prepared in Step 1 and mixed until completely dissolved and the solution was homogeneous. The cupric sulfate pentahydrate was then added and mixed until completely dissolved and the solution was homogeneous. Finally, the magnesium sulfate heptahydrate was then added and mixed until completely dissolved and the solution was homogeneous. Mixing was continued for 12 hours until an even consistency was obtained at room temperature.

Starting material considerations and alternatives: Starting materials to produce $NH_3$ or $NH_4^+$ in an aqueous solution are advantageously ammonium water (0.5-28%), ammonium sulfate or ammonium hydrogen sulfate and sulfamic acid by any method of manufacture known to those of ordinary skill in the art. Starting materials to produce $HSO_4^+$ in an aqueous solution are sulfuric acid (1.0-98% concentration) or sulfamic acid by any method known to those of ordinary skill in the art. Starting materials to produce any or all of the starting materials to produce metal hexa-aqua ions in an aqueous solution are any metal sulfate, metal nitrate, metal hydroxide, metal hydroxide/amine species, metal amine, metal chloride, metal iodide, metal bromide, metal carbonate, or metal carbonyl including, but not limited to, any combination of ligands stated.

Zinc Hexa-Aqua, Copper-Hexa-Aqua, Magnesium Hexa-Aqua and Selenous Acid Compositions:

Using the procedure of Example 1, the following ingredients are combined in the following w/w % ranges of component ions, depending on desired route of administration and application:

| Material | w/w % Minimum | w/w % Maximum |
|---|---|---|
| Sulfuric Acid | 1.00% | 4.50% |
| Ammonium Sulfate | 0.01% | 5.00% |
| Deionized Water | 35.00% | 75.00% |
| Zinc Sulfate Heptahydrate | 10.00% | 30.00% |
| Cupric Sulfate Pentahydrate | 5.00% | 10.00% |
| Magnesium Sulfate Heptahydrate | 10.00% | 30.00% |
| Selenium Oxide | 0.25% | 5.00% |

Example 3

Zinc Hexa-Aqua, Copper-Hexa-Aqua, Magnesium Hexa-Aqua and Selenous Acid Composition: ZCMS-AHS-5/2/1/1 in a 0.5 Kg Batch Following the procedure of Example 1, the ammonium sulfate is substituted with ammonium hydrogen sulfate to compensate for the non-reacted sulfuric acid in the reaction in Example 1. In Step 2 from Example 1, selenium dioxide is added first, in the same method as the other metal salts are added. This formulation is a more efficient one-batch synthesis using the method of Example 1, to produce the preferred composition shown below:

| Ingredient | Target metal ion mass percentage: | Ingredient mass (Kg) | Mass percentage (w/w %) |
|---|---|---|---|
| Sulfuric Acid | — | 0.01739 | 3.48% |
| Ammonium Hydrogen Sulfate | — | 0.00576 | 1.15% |
| Deionized Water Type 1 | — | 0.26991 | 53.98% |
| Zinc Sulfate Heptahydrate | 5.0% | 0.10992 | 21.98% |
| Cupric Sulfate Pentahydrate | 2.0% | 0.03929 | 7.86% |
| Magnesium Sulfate Heptahydrate | 1.0% | 0.05070 | 10.14% |
| Selenium Dioxide | 1.0% | 0.00704 | 1.41% |
| Total | — | 0.5000 | 100% |

Using the procedure of Example 1 and the modifications noted above, there is combined the following ingredients in the following w/w % ranges of component ions, depending on the preferred route of administration and application:

| Material | w/w % Minimum | w/w % Maximum |
|---|---|---|
| Sulfuric Acid | 0.50% | 4.50% |
| Ammonium Hydrogen Sulfate | 0.05% | 10.00% |
| Deionized Water | 35.00% | 80.00% |
| Zinc Sulfate Heptahydrate | 10.00% | 30.00% |
| Cupric Sulfate Pentahydrate | 5.00% | 10.00% |
| Magnesium Sulfate Heptahydrate | 10.00% | 30.00% |
| Selenium Oxide | 0.05% | 2.50% |

Example 4

Zinc Hexa-Aqua, Copper-Hexa-Aqua, Magnesium Hexa-Aqua, Manganese Hexa-Aqua, and Selenous Acid Composition:

ZCMMS-AHS-5/2/1/1/1 in a 0.5 Kg Batch

Using the procedure of Example 1, the ammonium sulfate is instead substituted with ammonium hydrogen sulfate and thereby will compensate for the non-reacted sulfuric acid reaction product of Example 1 when ammonium sulfate is used. In Step 2 of Example 1, the selenium dioxide is instead added in the same method as the other metal salts and is added first, and manganese sulfate is added second, after the selenous acid product is formed. This formulation is a more efficient one-batch synthesis of Example 1, to produce the preferred composition shown below:

| Ingredient | Target mass percentage inputs: | Batch mass (Kg) | Mass percentage (w/w %) |
|---|---|---|---|
| Sulfuric Acid | — | 0.01657 | 3.31% |
| Ammonium Hydrogen Sulfate | — | 0.00549 | 1.10% |
| Deionized Water Type 1 | — | 0.25726 | 51.45% |
| Zinc Sulfate Heptahydrate | 5.0% | 0.10992 | 21.98% |
| Cupric Sulfate Pentahydrate | 2.0% | 0.03929 | 7.86% |
| Magnesium Sulfate Heptahydrate | 1.0% | 0.05070 | 10.14% |
| Selenium Dioxide | 1.0% | 0.00703 | 1.41% |
| Manganese Sulfate anhydrous | 1.0% | 0.01374 | 2.75% |
| Total | — | 0.5000 | 100% |

Using the procedure of Example 1 and modifications described above, there is combined the following ingredients in the following w/w % ranges of component ions, depending on the desired route of administration and application:

| Material | w/w % Minimum | w/w % Maximum |
|---|---|---|
| Sulfuric Acid | 0.50% | 4.50% |
| Ammonium Hydrogen Sulfate | 0.05% | 10.00% |
| Deionized Water | 35.00% | 80.00% |
| Zinc Sulfate Heptahydrate | 8.00% | 25.00% |
| Cupric Sulfate Pentahydrate | 3.00% | 10.00% |
| Magnesium Sulfate Heptahydrate | 8.00% | 25.00% |
| Selenium Oxide | 0.05% | 5.00% |
| Manganese Sulfate anhydrous | 0.05% | 5.00% |

Example 5

Zinc Hexa-Aqua, Copper-Hexa-Aqua, Magnesium Hexa-Aqua Compositions

Using the procedure of Example 1, there is combined the following ingredients in the following w/w % ranges of component ions:

| Material | w/w % Minimum | w/w % Maximum |
|---|---|---|
| Deionized Water | 50.00% | 95.00% |
| Hydrogen Sulfate | 5.00% | 20.00% |
| Ammonium ion | 0.01% | 3.00% |
| Hexa-aqua zinc | 2.00% | 8.00% |
| Hexa-aqua copper | 1.00% | 3.00% |
| Hexa-aqua magnesium | 1.00% | 3.00% |
| Hydrogen cation | 0.01% | 0.50% |

The pharmaceutically acceptable salts of the compounds used in the compositions of the invention include the conventional non-toxic salts or the quaternary ammonium salts of said compounds formed, e.g., from non-toxic inorganic or organic acids, and for example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Generally, the salts are prepared by reacting the free base or acid with stoichiometric amounts or with an excess of the desired salt-forming inorganic or organic acid or bases in a suitable solvent or various combinations of solvents. The pharmaceutically acceptable salts are also readily prepared by conventional procedures such as treating an acid with an appropriate amount of a base, such as an alkaline or alkaline earth metal hydroxide e.g. sodium, potassium, lithium, calcium, or magnesium, or an organic base such as an amine, e.g., dibenzyl ethylenediamine, trimethylamine, piperidine, pyrrolidine, benzylamine and the like, or a quaternary ammonium hydroxide such as tetramethylammonium hydroxide and the like.

The compounds of Formula I, may be administered to animals, preferably to mammals, and most especially to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including by intravenous, intramuscular, intraperitoneal, subcutaneous, or topical administration. For oral use of a composition according to this invention, it may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled, to render the preparation isotonic. When a composition of the invention is used in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.005 mg/kg to about 50 mg/kg of body weight, and preferably, of from about 0.05 mg/kg to about 50 mg/kg of body weight, and most preferably, of from about 0.5 mg/kg to about 20 mg/kg of body weight, administered in single or divided doses.

An ordinarily skilled formulation scientist may modify the formulations within the specifications' teachings to provide numerous formulations for a particular administration route without rendering compositions containing IBAL unstable or compromising their therapeutic activity.

Example 6 a Zinc Hexa-Aqua, Copper-Hexa-Aqua, Magnesium Hexa-Aqua Composition Formulated into a Topical Gel Medicament The composition product of Example 1, Ion ZCM 1, as the active ingredient, was prepared in a dermatological gel formulation for topical administration at a concentration of 25% w/w, comprising:

| Ingredient | Amount |
|---|---|
| Purified Water | 0.6625 gm |
| Ion ZCM 1 | 0.250 gm |
| SEPINEO DERM | 0.043 gm |
| Sodium Hyaluronate PC | 0.020 gm |
| Glycerin | 0.020 gm |
| Sodium Hydroxide | 0.005 gm |

| Ingredient | Amount |
|---|---|
| Purified Water | 0.665 gm |
| Ion ZCM 1 | 0.250 gm |
| SEPINIO D.E.R.M. | 0.040 gm |
| Sodium Hyaluronate PC | 0.020 gm |
| Glycerin | 0.020 gm |
| Sodium Hydroxide | 0.005 gm |

SEPINIO™ D.E.R.M. is a multi-functional powder polymer manufactured by SEPPIC, CAS number 111286-86-3, used for thickening, stabilizing/emulsifying, co-stabilizing and texturizing all dosage forms. This polymer needs no neutralization, works at all pH and enables room-temperature manufacturing. It is composed of hydroxyethyl acrylate, sodium acryloyl dimethyl taurate copolymer, and may function as a co-stabilizer, emulsifier-stabilizer, texturizing agent, thickener, topical excipient, and viscosity agent.

Example of the Formulation of a 1 kg Batch of Ion Gel ZCM-25

To 0.5625 kg of deionized water was slowly added the Sepineo Derm, then stirred with a teflon-coated marine propeller at 500 rpm until the Sepineo Derm had hydrated completely, as demonstrated when no lumps were observed. The sodium hyaluronate PC was added and stirred at 500 rpm until a homogeneous mixture was obtained. The glycerin was added and mixed at 500 rpm until a homogeneous mixture was obtained. In a glass beaker, the sodium hydroxide was dissolved in 10% purified water (0.1 kg of purified water for 1 kg of Ion Gel ZCM-25. The sodium hydroxide solution was added to the mixture and stirred at 500 rpm until homogenized, pausing and stirring between each successive addition. The Ion ZCM-1 was added and stirred at 750 rpm until the mixture appeared homogeneous and no lumps or discolorations were observed. The pH of the product was measured, and sodium hydroxide solution was added until the observed pH was 2.0. Ion Gel ZCM-25—Production Process (Laboratorios Manuell, 2020). Product analysis:

| Determination | Specifications | Result | Reference |
|---|---|---|---|
| Color | Sky blue | | |
| Odor | Odorless | | |
| pH | 1.0 to 2.5 | 2.26 | FEUM 12 Ed. MGA 0701 pages 493-494 |
| Zinc ion identification | Presence of a white precipitate | Compliant | FEUM 12 Ed. MGA 0701 page 441 |
| Copper ion identification | Formation of a blue precipitate | Compliant | FEUM 12 Ed. MGA 0511 page 438 |
| Magnesium ion identification | Formation of a white crystalline precipitate | Compliant | FEUM 12 Ed. MGA 0511 page 439 |
| Ion evaluation | Copper ion: >0.025 to 0.063 gm Cu | Compliant | USP 29-NF 24 Page 602 |
| Viscosity | To be in a range of 7,960 to 8,040 cP | 8.030.67 cP | FEUM 12 Ed. MGA 0951 pages 520-523 |

Example 7

A Copper Hexa-Aqua, Zinc Hexa-Aqua Composition

| Material/ Reagent | Name | Formula | CAS Number | Mass Concentration range w/w % | Molar Concentration |
|---|---|---|---|---|---|
| 1 | Hexa-aqua Copper (II) Ion | $Cu(H_2O)_6^{2+}$ (aq) | none | 2.33% | 433 mM |
| 2 | Hexa-aqua Zinc (II) Ion | $Zn(H_2O)_6^{2+}$ (aq) | none | 7.2% | 1300 mM |
| 3 | Hydrogen Cation | $H^+$ (aq) | none | 0.1% | 1120 mM |
| 4 | Ammonium | $NH_4^+$ (aq) | 14798-03-9 | 1.43% | 933 mM |
| 5 | Hydrogen Sulfate | $HSO_4^-$ (aq) | 14996-02-2 | 19.31% | 2350 mM |
| 6 | Water | $H_2O$ | 7732-18-5 | 69.64% | — |

Example 8

A Hexa-Aqua Delivery System of Zinc, Magnesium, and Copper Coordinated Complexes

| Material/ Reagent | Name | Formula | CAS Number | Mass Concentration range w/w % |
|---|---|---|---|---|
| 1 | Hexa-aquaCopper (II) Ion | $Cu(H_2O)_6^{2+}$ (aq) | none | 1.00-3.00% |
| 2 | Hexa-aquaZinc (II) Ion | $Zn(H_2O)_6^{2+}$ (aq) | none | 2.00-8.00% |
| 3 | Hexa-aquaMagnesium (II) Ion | $Mg(H_2O)_6^{2+}$ (aq) | none | 1.00-3.00% |
| 4 | Hydrogen Cation | $H^+$ (aq) | none | 0.01-0.5% |
| 5 | Ammonium | $NH_4^+$ (aq) | 14798-03-9 | 0.10-3.00% |
| 6 | Hydrogen Sulfate | $HSO_4^-$ (aq) | 14996-02-2 | 5.00-28.00% |
| 7 | Water | $H_2O$ | 7732-18-5 | 50-95% |

Example 9

A Copper Hexa-Aqua, Zinc Hexa-Aqua, Magnesium Hexa-Aqua Composition

| Material/ Reagent | Name | Formula | CAS Number | Mass Concentration range w/w % | Molar Concentration |
|---|---|---|---|---|---|
| 1 | Hexa-aquaCopper (II) Ion | $Cu(H_2O)_6^{2+}$ (aq) | none | 2.39% | 444 mM |
| 2 | Hexa-aquaZinc (II) Ion | $Zn(H_2O)_6^{2+}$ (aq) | none | 7.2% | 1300 mM |
| 3 | Hydrogen Cation | $H^+$ (aq) | none | 0.1% | 1120 mM |
| 4 | Ammonium | $NH_4^+$ (aq) | 14798-03-9 | 1.43% | 933 mM |
| 5 | Hydrogen Sulfate | $HSO_4^-$ (aq) | 14996-02-2 | 19.31% | 2350 mM |
| 6 | Water | $H_2O$ | 7732-18-5 | 69.64% | |

Figure 2:
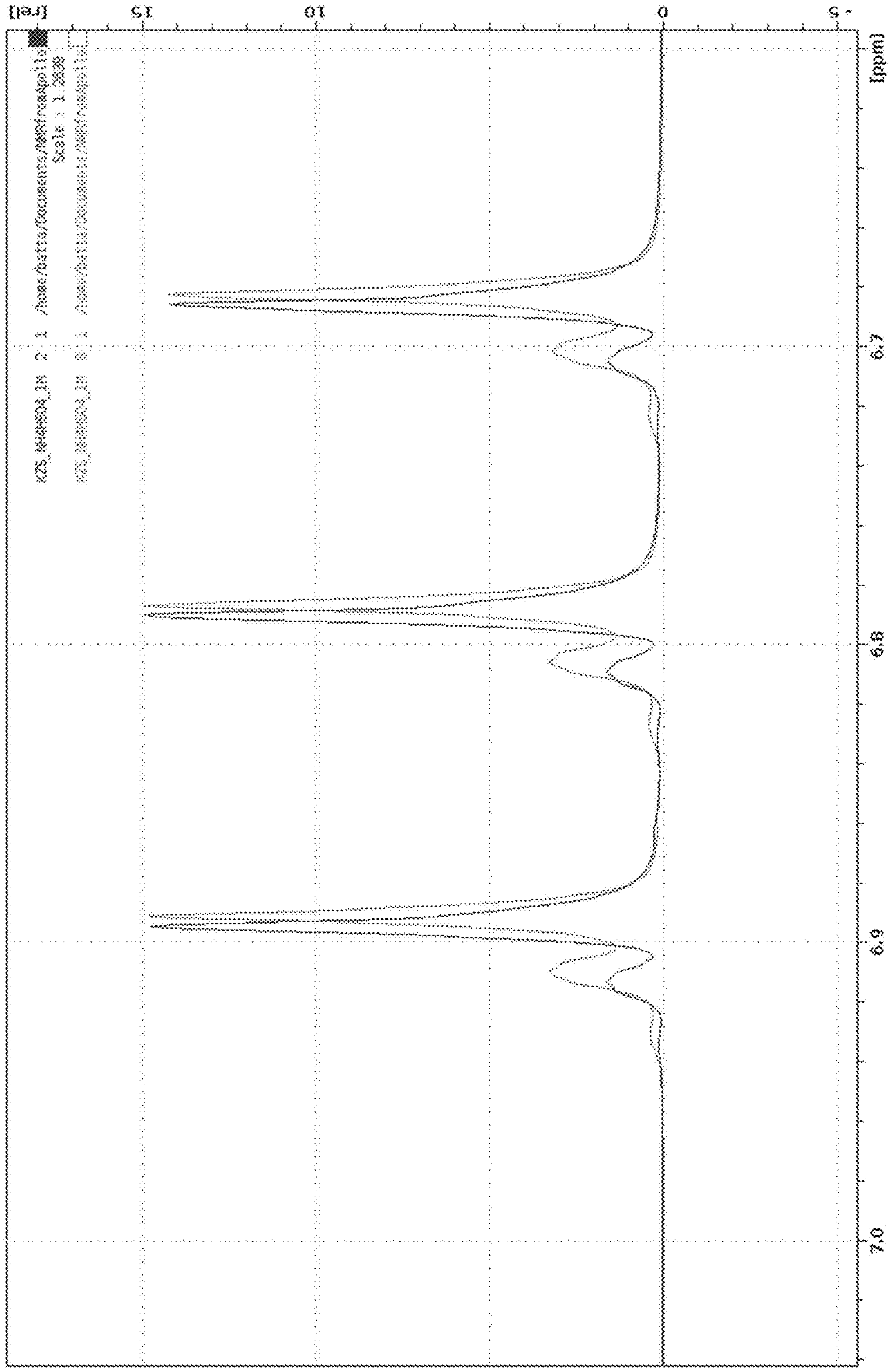
FIG. 2 is an NMR spectrum generated at ca. 100 mM $NH_4{}^+$ in the presence of 5 and 10% $D_2O$.
Figure 3:
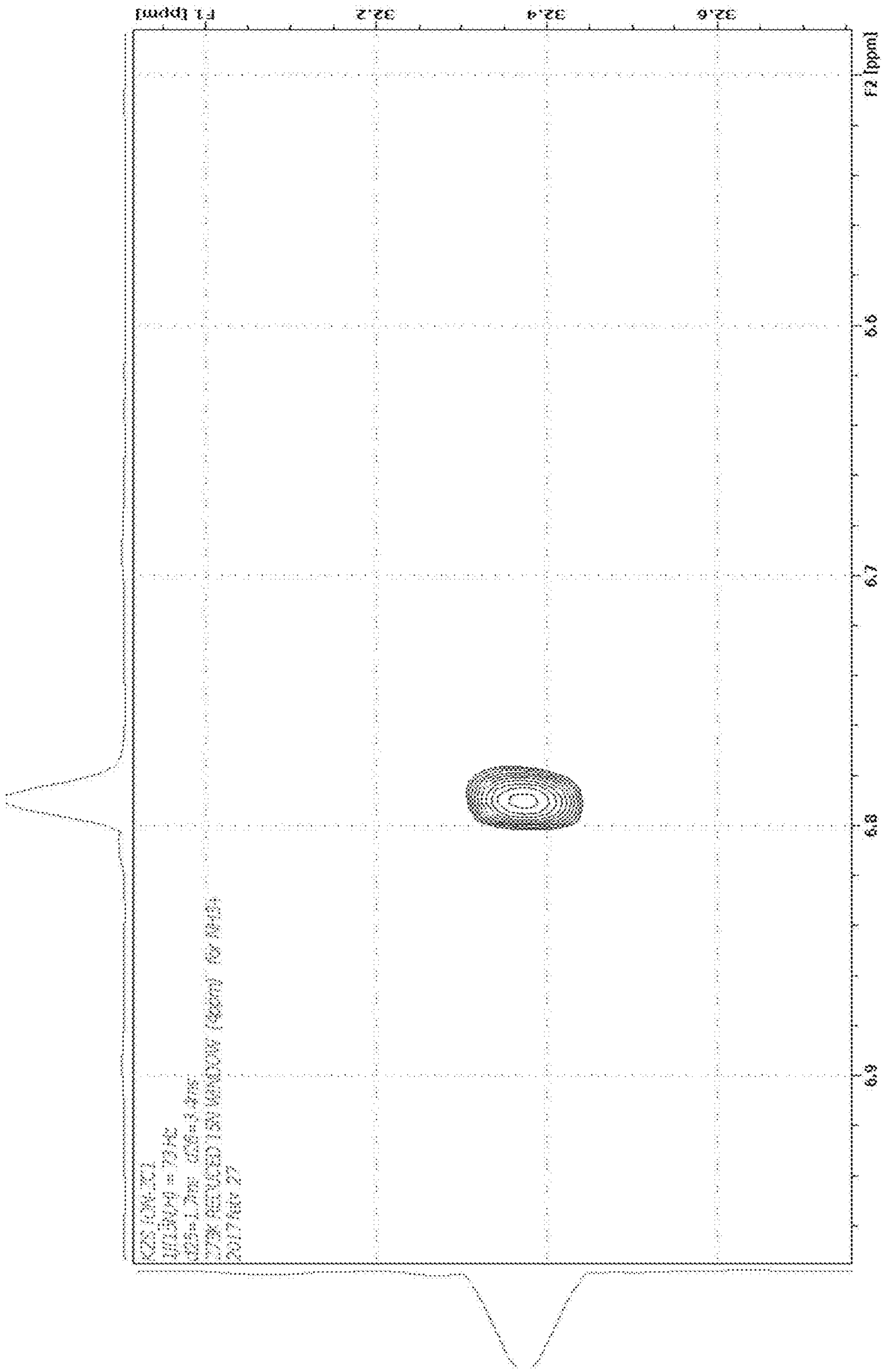
FIG. 3 is an NMR spectrum generated at $^{15}$N-$^1$H in 2D HISQC spectrum of a solution containing 100 mM $NH_4{}^+$.

NMR Analysis of the Composition of Example 8, ZC-1. NMR studies verified the presence of dominant $NH_4^+$ ammonium ions. The NMR studies were conducted as follows. An original stock solution was diluted 100 times using a $H_2O/D_2O$ 95/5% w/w solvent and $^1H$ NMR spectra, with watergate water suppression technique, were collected first at 275 K temperature, to slow down anticipated chemical exchange effects. The first spectra showed well resolved triplets with equal intensity of lines of 52 Hz splittings at 6.82 ppm chemical shift, with an assumed water reference at 4.7 ppm. At the same time, there were observed low intensity satellites to the left from the main lines, well separated from the main triplet, that exhibited triplet-like structure with small, 1.3-1.4 Hz splittings. Raising the temperature in two steps to 298 K and 320 K proved the exchange hypothesis. Referring to FIG. 1, the slow exchange between $NH^4$+ protons and solvent water were increased by temperature, that caused first line broadening and then coalescence of the two "species" into a single broad line. The explanation of the triplet is that in a slowly exchanging system, the four equivalent protons show spin-spin coupling to the $^{14}N$ nucleus. Since the nuclear spin of $^{14}N$ is I=1, the proton lines were split to a triplet. The small satellites at the foot of the signals were explained take into account the presence of ca. 5% $D_2O$ in the solution. Then, $^{14}NH_3D$+ groups were formed due to an exchange with water that resulted in the pop-up of the three extra signal, with the isotope shifted from main signals. Their small triplets were due to the coupling of three equivalent protons to one deuterium of spin 1. To double check the deuterium isotope shift effect, a solution was prepared, containing 1M $NH+^4$ ammonium ion. 50 µl of this solution was extended by 425 µl $H_2O$ and 25 µl $D_2O$ for NMR. Then an additional 25 µl $D_2O$ was added. The two resulting spectra are shown in FIG. 2, where it is seen that the amount of $^{14}NH_3D^+$ satellites has doubled. In the presence of 10% $D_2O$ there are also visible the new deuterium satellite signals of $^{14}NH_2D_2^+$, due to further deuteration. There, multiplicity is five, due to two deuterons: m=2nI+1=2*2*1+1=5. The concentration of this solution allowed the observation of the low natural abundance $^{15}N$ signals in 2D HISQC experiment (16 hrs. acquisition at 273 K). This spectrum is shown in FIG. 3. The $^{15}N$ chemical shift is 32.4 ppm, which accorded with the predicted expected values for $^{15}NH_4^+$ (for charged Lysine $NH_3^+$ groups this is also around 32 ppm in proteins).

Figure 4:
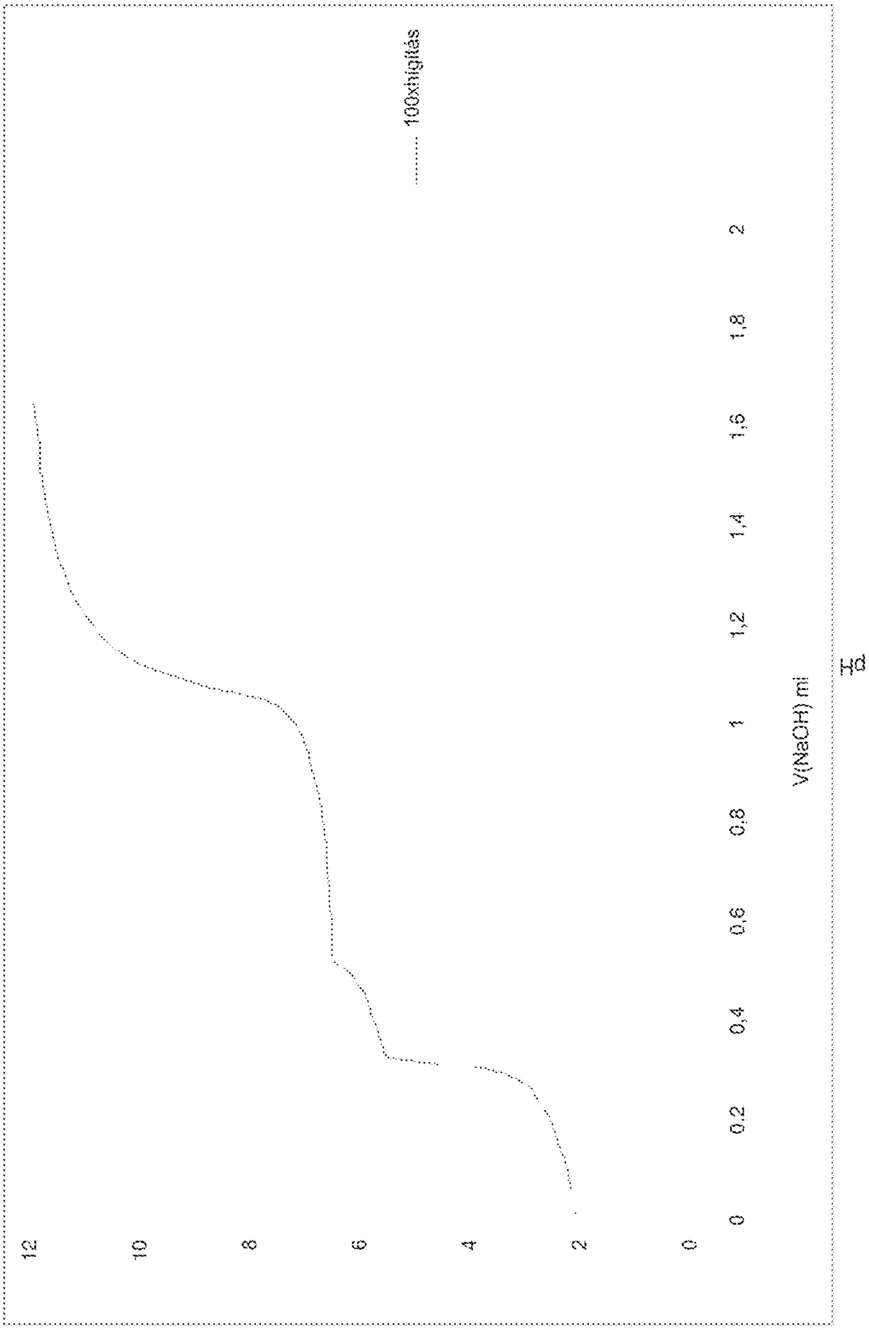
FIG. 4 is a graph of a titration curve showing the overall acid content of a pH-potentiometric titration.

Acid Content of the Stock Solution. Using direct potentiometry: a 100-fold serial dilution was performed, and the pH was measured finding a pH=2.3, indicating that even the diluted sample was also highly acidic. To measure the overall acid content, a pH-potentiometric titration was carried out. A 600 µL of stock acid solution was diluted to 6 mL, and the sample was titrated by 0.2115 µmol/dm3 NaOH solution. The resulting titration curve shown at FIG. 4 showed three inflection points. The first one, $H^++NaOH=Na^++H_2O$, at 0.3127 ml was attributed to the base-consumption of a strong acid ($HSO_4^-$) in the sample, yielding a 1.12 mol/$dm^3$ concentration in the stock acid solution. The second (less characteristic) pH-change, with an inflection point at about 0.509 ml was related to the formation of barely soluble metal-hydroxides, which is characteristic for Cu(II) and Zn(II) in a pH range near neutral. The sample is not homogenous in the pH=6-8 range. This phenomenon is well known for $Cu^{2+}$ and $Zn^{2+}$ and the reaction can be exemplified by the reaction as: $2CuSO_4$+2NaOH═$Cu_2(OH)_2(SO_4)$+$Na_2SO_4$, where the underlining indicated the formation of a solid precipitate. The third pH jump is related to the deprotonation of the $NH_4^+$ ions: $NH_4^+$+NaOH=$NH_3$+$Na^+$+$H_2O$ The free ammonia ($NH_3$) is a good ligand for both $Cu^{2+}$ and $Zn^{2+}$ cations. The reaction of the complex formation is as follows: $Cu^{2+}$+$4NH_3$ □[Cu $(NH_3)_4]^{2+}$ The formation of the tetra-amine complex results in the dissolution of the precipitates and a clear, bluish (azure) solution. The analogous tetra-amine zinc complex [Zn $(NH_3)_4]^{2+}$ is colorless. The difference between the first and the third inflection point (1.06−0.31=0.76 ml) gives $CuNH_4^+$=2.69 μmol/$dm^3$ in the stock solution.

Example 10 a Copper Hexa-Aqua, Zinc Hexa-Aqua, Magnesium Hexa-Aqua, Selenous Acid, and Manganese Hexa-Agua Composition

| No. | Name | Formula | CAS Number | Mass Concentration range w/w % |
|---|---|---|---|---|
| 1 | Hexa-aqua Copper (II) Ion | $Cu(H_2O)_6^{2+}$ (aq) | none | 1.00-3.00% |
| 2 | Hexa-aqua Zinc (II) Ion | $Zn(H_2O)_6^{2+}$ (aq) | none | 2.00-8.00% |
| 3 | Hexa-aqua Magnesium (II) Ion | $Mg(H_2O)_6^{2+}$ (aq) | none | 1.00-3.00% |
| 3 | Selenium Oxide dihydroxide (IV) Ion | $SeO(HO)_2^{4+}$ (aq) | 7783-00-8 | 0.10-2.00% |
| 3 | Hexa-aqua Manganese (II) Ion | $Mn(H_2O)_6^{2+}$ (aq) | none | 0.10-3.00% |
| 4 | Hydrogen Cation | $H^+$ (aq) | none | 0.01-0.5% |
| 5 | Ammonium | $NH_4^+$ (aq) | 14798-03-9 | 0.01-3.00% |
| 6 | Hydrogen Sulfate | $HSO_4^-$ (aq) | 14996-02-2 | 5.00-28.00% |
| 7 | Water | $H_2O$ | 7732-18-5 | 50-95% |

Metal ratios are 5 Zn:2 Cu:1 Mg:0.5 Se:0.5 M

Example 11

A Copper (II) Hexa-Aqua, Zinc (II) Hexa-Aqua, Magnesium (II) Hexa-Aqua Composition

| Material/ Reagent | Name | Formula | CAS Number | Mass Concentration range w/w % |
|---|---|---|---|---|
| 1 | Hexa-aqua Copper (II) Ion | $Cu(H_2O)_6^{2+}$ (aq) | none | 1.00-2.50% |
| 2 | Hexa-aqua Zinc (II) Ion | $Zn(H_2O)_6^{2+}$ (aq) | none | 3.50-5.00% |
| 3 | Hexa-aqua Magnesium (II) Ion | $Mg(H_2O)_6^{2+}$ (aq) | none | 1.00-2.50% |
| 4 | Hydrogen Cation | $H^+$ (aq) | none | 0.01-3.00% |
| 5 | Ammonium | $NH_4^+$ (aq) | 14798-03-9 | 0.05-3.00% |
| 6 | Hydrogen Sulfate | $HSO_4^-$ (aq) | 14996-02-2 | 18.00-20.00% |
| 7 | Water | $H_2O$ | 7732-18-5 | 70.0%-71.5% |

Example 12

A Copper (II) Hexa-Aqua, Zinc (II) Hexa-Aqua Composition

| Material/ Reagent | Name | Formula | CAS Number |
|---|---|---|---|
| 1 | Hexa-aqua copper (II) Ion | $Cu(H_20)_6^{2+}$ | None |
| 2 | Hexa-aqua zinc (II) Ion | $Zn(H_20)_6^{2+}$ | None |
| 3 | Hydrogen Cation | $H^+$ | None |
| 4 | Ammonium | $NH_4^+$ | 14798-03-9 |
| 5 | Hydrogen Sulfate | $HSO_4^-$ | 14996-02-2 |
| 6 | Water | $H_20$ | 7732-18-5 |

Example 13

Redox Potential Assay

A Redox Potential Assay of ZCM-1 was measured at 453.2 mV using method SM2580B

Example 14

Oxygen Radical Absorbance Capacity (ORAC) Activity Assay ION ZCM-1 Yielded ORAC Values of:

Total ORAC=H-ORAC value of 1138 μM TE/100 g

Total ORAC value for [ION-ZCM1] is 1025 μM TE/ml when measured at a dilution of 12.5%

Total ORAC value for [ION-ZCM1] is 740 μM TE/ml when measured at a dilution of 6.25%

Comparators:

Total ORAC value for Vitamin E is 580 to 585 μmol TE/g at 1:1

Total ORAC value for Vitamin C is 128 to 133 μmol TE/g at 1:1

Total ORAC value for Pepper Leaf Extract is 64.47 μmol TE/g at 1:50 or approximately a 2% solution.

Materials and methods disclosed at INDEVION Biotechnology Research and Development. (2018). *ORAC Study of Antioxidant Capabilities*. University of Debrecen, Dept. Microbial Biotechnology and Cell Biology, Faculty of Natural Sciences and Technology. Debrecen, Hungary: Dr. Zsolt Keresztessy, PhD, MBA. Retrieved 2021 from https://drive.google.com/file/d/1HDhtRcW9D-F-dKDuA-YxnQWukne3UnC0/view?usp=sharing, the entire disclosure of which is incorporated herein by reference.

Example 15

Anti-Tumor Efficacy Studies in Mouse Melanoma

The compositions of the invention attack a multitude of cancer pathways. Three specific in-vitro and in-vivo preclinical studies have shown anti-cancer activities of ZC-1.

A first study concluded the following: (Anti-Tumor Efficacy Study by Intravenous Injection—B16 Mouse Melanoma—30 Mice. Completed in 2016 by the University of Debrecen, Hungary) that safety abnormalities compared to control tumor mice were not noted for any of the animals when necropsied at the conclusion of the 14-day observation period.

Histopathology: tumors isolated from mice treated with various concentrations of the invention by IV injections show massive necrosis, which is not pronounced as much in tumors isolated from control tumor mice; blood vessels were much less frequent, and less developed in the invention-treated mice compared to control tumor mice; and invention composition by injection resulted in spleen enlargement, which is remarkably (2-3 times) bigger in extent than that of the spleen of control (untreated) tumor mice and was consistent with the invention inducing a strong anti-tumor immune response.

A second study concluded the following: (Topical Cream Anti-Tumor Efficacy Study—Syngeneic Mouse Melanoma—30 Mice. Completed in 2017 by the University of Debrecen, Hungary); the invention composition formulated in a topical cream (17%) was significantly efficacious against metastatic mouse melanoma as tested in a subcutaneous syngeneic mouse model (B16-F0 in C57BL/6J mice); was more efficacious than Imiquimod Topical Cream (5%); showed that tumor volumes recorded over the treatment period in the three animal model groups supported the observation that tumor growth was slower, having been inhibited by the invention composition topical cream (17%), and its effect was more pronounced when compared to the inhibitory effect of ALDARA® (5% Imiquimod), the positive control substance, on tumor growth; and that the invention composition topical cream (17%) treatment extended survival time.

A third study concluded the following: that the invention composition formulated in a solution was a responsive cytotoxic agent against renal carcinoma cell line Caki-1 (IC50 36.12±1.00 μM), in triple negative breast cancer (MDA-MB-231), and melanoma cancer cell line A375 (IC50 95.20±1.01 μM) while also highly selective when compared to the cytotoxicity of the invention composition on control cells IMR-90 (IC50 142.6±6.65 μM); and that the invention composition in solution form induced apoptotic death in 92% of renal carcinoma cell line Caki-1 at dose IC50 36.12±1.00 μM.

Example 16

Antimicrobial Activity of ZC-1

| ZC-1 | Product Concentration | Type of Study | Pathogen Type | Pathogen Code | Pathogen Name | Test Method |
|---|---|---|---|---|---|---|
| ZC-1 | 1.063% v/v | Broth Microdilution | Gram N- Bacteria | ATCC 25922 | *ESCHERICHIA COLI* | CLSI-BMD |
| ZC-1 | 0.354% v/v | Broth Microdilution | Gram P- Bacteria | ATCC 29213 | *STAPHYLOCOCCUS AUREUS* | CLSI-BMD |
| ZC-1 | 2.125% v/v | Broth Microdilution | Gram N- Bacteria | ATCC 27583 | *PSEUDOMONAS AERUGINOSA* | CLSI-BMD |
| ZC-1 | 1.063% v/v | Broth Microdilution | Gram N- Bacteria | ATCC 70603 | *KLEBSIELLA PNEUMONIAE* | CLSI-BMD |
| ZC-1 | 0.531% v/v | Broth Microdilution | Gram N- Bacteria | ATCC 29212 | *ENTEROCOCCUS FAECALIS* | CLSI-BMD |
| ZC-1 | 1.063% v/v | Broth Microdilution | Gram N- Bacteria | ATCC 61370 | *PROTEUS MIRABILIS* | CLSI-BMD |
| ZC-1 | 0.133% v/v | Broth Microdilution | Fungus | ATCC 10231 | *CANDIDA ALBICANS* | CLSI-BMD |
| ZC-1 | <0.008% v/v | Broth Microdilution | Fungus | ATCC 90030 | *CANDIDA GLABRATA* | CLSI-BMD |
| ZC-1 | 0.0170% v/v | Broth Microdilution | Fungus | ATCC 22019 | *CANDIDA PARAPSILOSIS* | CLSI-BMD |
| ZC-1 | 0.1773% v/v | Broth Microdilution | Fungus | ATCC 750 | *CANDIDA TROPICALIS* | CLSI-BMD |
| ZC-1 | 0.0330% v/v | Broth Microdilution | Fungus | ATCC 20446 | *SACCHAROMYCES CEREVISIAE* | CLSI-BMD |

| ZC-1 | Pathogen Name | Test Time | Test Count | Kill Rate |
|---|---|---|---|---|
| ZC-1 | *ESCHERICHIA COLI* | 24 Hours | 1 × 10^3 CFU/mL | 50% Turbidity Reduced |
| ZC-1 | *STAPHYLOCOCCUS AUREUS* | 24 Hours | 1 × 10^3 CFU/mL | 50% Turbidity Reduced |
| ZC-1 | *PSEUDOMONAS AERUGINOSA* | 24 Hours | 1 × 10^3 CFU/mL | 50% Turbidity Reduced |
| ZC-1 | *KLEBSIELLA PNEUMONIAE* | 24 Hours | 1 × 10^3 CFU/mL | 50% Turbidity Reduced |
| ZC-1 | *ENTEROCOCCUS FAECALIS* | 24 Hours | 1 × 10^3 CFU/mL | 50% Turbidity Reduced |
| ZC-1 | *PROTEUS MIRABILIS* | 24 Hours | 1 × 10^3 CFU/mL | 50% Turbidity Reduced |
| ZC-1 | *CANDIDA ALBICANS* | 24 Hours | 1 × 10^3.5 CFU/mL | 50% Turbidity Reduced |
| ZC-1 | *CANDIDA GLABRATA* | 24 Hours | 1 × 10^3.5 CFU/mL | 50% Turbidity Reduced |
| ZC-1 | *CANDIDA PARAPSILOSIS* | 24 Hours | 1 × 10^3.5 CFU/mL | 50% Turbidity Reduced |
| ZC-1 | *CANDIDA TROPICALIS* | 24 Hours | 1 × 10^3.5 CFU/mL | 50% Turbidity Reduced |
| ZC-1 | *SACCHAROMYCES CEREVISIAE* | 24 Hours | 1 × 10^3.5 CFU/mL | 50% Turbidity Reduced |

Example 17

MRSA Antimicrobial Activity of ZC-1

| ZC-1 | Product Concentration | Type of Study | Pathogen Type | Pathogen Code | Pathogen Name | Test Method |
|---|---|---|---|---|---|---|
| " | 0.425% v/v | Broth Microdilution | Gram P- Bacteria | ATCC 43032 | *Staphylococcus aureus* (MRSA) | CLSI-BMD |
| " | 0.212% v/v | Broth Microdilution | Gram P- Bacteria | ATCC 43088 | *Staphylococcus aureus* (MRSA) | CLSI-BMD |
| " | 0.212% v/v | Broth Microdilution | Gram P- Bacteria | ATCC 43072 | *Staphylococcus aureus* (MRSA) | CLSI-BMD |
| " | 0.212% v/v | Broth Microdilution | Gram P- Bacteria | ATCC 42631 | *Staphylococcus aureus* (MRSA) | CLSI-BMD |
| " | 0.212% v/v | Broth Microdilution | Gram P- Bacteria | ATCC 42762 | *Staphylococcus aureus* (MRSA) | CLSI-BMD |
| " | 0.212% v/v | Broth Microdilution | Gram P- Bacteria | ATCC 43167 | *Staphylococcus aureus* (MRSA) | CLSI-BMD |
| " | 0.212% v/v | Broth Microdilution | Gram P- Bacteria | ATCC 43100 | *Staphylococcus aureus* (MRSA) | CLSI-BMD |
| " | 0.425% v/v | Broth Microdilution | Gram P- Bacteria | ATCC 43221 | *Staphylococcus aureus* (MRSA) | CLSI-BMD |
| " | 0.212% v/V | Broth Microdilution | Gram P- Bacteria | ATCC 42472 | *Staphylococcus aureus* (MRSA) | CLSI-BMD |
| " | 0.425% v/v | Broth Microdilution | Gram P- Bacteria | ATCC 12890 | *Staphylococcus aureus* (MRSA) | CLSI-BMD |

| ZC-1 | Pathogen Name | Test Time | Test Count | Kill Rate |
|---|---|---|---|---|
| " | *Staphylococcus aureus* (MRSA) | 24 Hours | 1 × 10^3 CFU/mL | 50% Turbidity Reduced |
| " | *Staphylococcus aureus* (MRSA) | 24 Hours | 1 × 10^3 CFU/mL | 50% Turbidity Reduced |
| " | *Staphylococcus aureus* (MRSA) | 24 Hours | 1 × 10^3 CFU/mL | 50% Turbidity Reduced |
| " | *Staphylococcus aureus* (MRSA) | 24 Hours | 1 × 10^3 CFU/mL | 50% Turbidity Reduced |
| " | *Staphylococcus aureus* (MRSA) | 24 Hours | 1 × 10^3 CFU/mL | 50% Turbidity Reduced |
| " | *Staphylococcus aureus* (MRSA) | 24 Hours | 1 × 10^3 CFU/mL | 50% Turbidity Reduced |
| " | *Staphylococcus aureus* (MRSA) | 24 Hours | 1 × 10^3 CFU/mL | 50% Turbidity Reduced |
| " | *Staphylococcus aureus* (MRSA) | 24 Hours | 1 × 10^3 CFU/mL | 50% Turbidity Reduced |
| " | *Staphylococcus aureus* (MRSA) | 24 Hours | 1 × 10^3 CFU/mL | 50% Turbidity Reduced |
| " | *Staphylococcus aureus* (MRSA) | 24 Hours | 1 × 10^3 CFU/mL | 50% Turbidity Reduced |

Example 18

Antimicrobial Activity of ION ZCM-1

| ION-ZCM-1 | Product Concentration | Type of Study | Pathogen Type | Pathogen Code | Pathogen Name | Test Method |
|---|---|---|---|---|---|---|
| " | 100% | Microbial challenge | Gram N. Bacteria | ATCC 15442 | *Pseudomonas aeruginosa* | AOAC 17th Ed. Cap.6 page 10 |
| " | 100% | Microbial challenge | Gram P. Bacteria | ATCC 6538 | *Staphyloccoccus aureus* | NMX-BB-040-SCFI-1999 |
| " | 100% | Microbial challenge | Gram N. Bacteria | ATCC 11229 | *Escherichia coli* | NMX-BB-040-SCFI-1999 |

| ION ZCM-1 | Pathogen Name | Test Time | Test Count | Kill Rate |
|---|---|---|---|---|
| " | Gram N. Bacteria | 30 seconds | 0 UFC/M1 | >120 000 000 UFC/mL; 100% |
| " | Gram P. Bacteria | 30 seconds | 0 UFC/M1 | >87 000 000 UFC/mL; 100% |
| " | Gram N. Bacteria | 30 seconds | 0 UFC/M1 | >110 000 000 UFC/mL; 100% |

Example 19

Antimicrobial Activity of the Product of ION GEL ZCM-25

| ION GEL ZCM-25 | Product Concentration | Type of Study | Pathogen Type | Pathogen Code | Pathogen Name | Test Method |
|---|---|---|---|---|---|---|
| " | 25% | Microbiological analysis | Gram+ bacteria Gram− bacteria | Not available | *Staphyloccoccus aureus* *Pseudomonas aeruginosa* | FEUM 12a. Ed. Page 464 |
| " | 25% | Microbiological analysis | Gram+ bacteria Gram− bacteria | Not available | *Staphyloccoccus aureus* *Pseudomonas aeruginosa* | FEUM 12a. Ed. Page 464 |
| " | 25% | Microbiological analysis | Gram+ bacteria Gram− bacteria | Not available | *Staphyloccoccus aureus* *Pseudomonas aeruginosa* | FEUM 12a. Ed. Page 464 |
| " | 25% | Microbiological analysis | Gram+ bacteria Gram− bacteria | Not available | *Staphyloccoccus* aureus *Pseudomonas aeruginosa* | FEUM 12a. Ed. Page 464 |
| " | 25% | Microbial challenge | Gram N. Bacteria | ATCC 15442 | *Pseudomonas aeruginosa* | AOAC 17th Ed. Cap.6 page 10 |
| " | 25% | Microbial challenge | Gram P. Bacteria | ATCC 6538 | *Staphyloccoccus* aureus | NMX-BB-040- |
| " | 25% | Microbial challenge | Gram N. Bacteria | ATCC 11229 | *Escherichia coli* | NMX-BB-040-SCFI-1999 |
| " | 25% | Microbiological analysis | *Mesofflicos aeróbios* | Not available | *Mesofflicos aeróbios* | FEUM 12a. Ed. Page 464 |
| " | 25% | Microbiological analysis | *Hongos y levaduras* | Not available | *Hongos y levaduras* | FEUM 12a. Ed. Page 464 |
| " | 25% | Microbiological analysis | Gram+ bacteria | Not available | *Staphyloccoccus aureus* | FEUM 12a. Ed. Page 464 |
| " | 25% | Virucidal activity test (Equine arteritis) | Virus | ATCC VR-796 | SARS CoV-2 | E 1053-97 |
| " | 25% | Microbial activity test (MRSA) | Bacterium | ATCC 33591 | MRSA | E 1053-97 |
| " | 25% | Fungicidal activity test (*Aspergillus*) | Fungus | ATCC 16404 | *Aspergillus brasiliensis* | E 1053-97 |

| ION GEL ZCM-25 | Pathogen Name | Test Time | Test Count | Kill Rate |
|---|---|---|---|---|
| " | *Staphyloccoccus aureus* *Pseudomonas aeruginosa* | NA | 0 UFC/M1 0 UFC/M1 | 100.00% 100.00% |
| " | *Staphyloccoccus ureus* *Pseudomonas aeruginosa* | NA | 0 UFC/M1 0 UFC/M1 | 100.00% 100.00% |
| " | *Staphyloccoccus aureus* *Pseudomonas aeruginosa* | NA | 0 UFC/M1 0 UFC/M1 | 100.00% 100.00% |
| " | *Staphyloccoccus aureus* *Pseudomonas aeruginosa* | NA | 0 UFC/M1 0 UFC/M1 | 100.00% 100.00% |
| " | *Pseudomonas aeruginosa* | 30 seconds | 0 UFC/M1 | >120 000 000 UFC/mL; 100% |
| " | *Staphyloccoccus aureus* | 30 seconds | 0 UFC/M1 | >87 000 000 UFC/mL; 100% |
| " | *Escherichia coli* | 30 seconds | 0 UFC/M1 | >110 000 000 UFC/mL; 100% |
| " | Microbiological analysis | NA | <10 UFC/g | 100.00% |
| " | Microbiological analysis | NA | <10 UFC/g | 100.00% |
| " | Microbiological analysis | NA | 0 UFC/M1 | 100.00% |
| " | Virucidal activity test (*Equine arteritis*) | 10 minutes | <20 Remaining Viral Titre | 99.9999% |
| " | Microbial activity test (MRSA) | 30 seconds | 1'200,000 | 99.990% |
| " | Fungicidal activity test (*Aspergillus brasiliensis*) | 30 seconds | 25,000 | 99.9561% |

Example 20

Biofilm Reduction Activity of the Product of ZC-1 IDC-49 T2

| ZC-1 | Product Concen-tration | Type of Study | Pathogen Type | Pathogen Code | Pathogen Name | Test Method |
|---|---|---|---|---|---|---|
| " | 6.25% | Broth Micro-dilution | Biofilm | ATCC22953 | Bioflim | CLSI-BMD |

| ZC-1 | Pathogen Name | Test Time | Test Count | Kill Rate |
|---|---|---|---|---|
| " | Biofilm | 24 hours | 1 × 10^3 CFU/mL | 50% Turbidity Reduced |

Example 21

Anti-MRSA Activity of ZC-1

A non-biofilm antimicrobial assay using the broth microdilution-based sensitivity method was completed at the University of Debrecen, Hungary. The results showed that minimum inhibitory concentration (MIC) values for ZC-1 against the 10-methicillin-resistant *Staphylococcus aureus* isolate tested were in the range of 0.212-0.85% (v/v). The Control for Vancomycin MIC values was in the range of 4-16 mg/L. The study compares the average MIC value of Example 6 of 0.531% (v/v) with the average MIC value of 10 mg/L for vancomycin. A percentage solution calculation established that twice the amount of vancomycin was needed to create the same 50% turbidity reduction in MRSA when tested in comparison to ZC-1.

Example 22

Safety Studies

| Study | Composition | Title | Result |
|---|---|---|---|
| A | ZC-1 | Acute Intravenous Toxicity in Mice | Non-toxic at test dosage of 667 mg/kg mouse body weight |
| B | ION ZCM-1 | Cell-based in Vitro Cytotoxicity | By a HACAT human cell line-based, the MTT Cytotoxicity test method established a safety profile for topical use at up to 25% concentration. |
| C | ION GEL ZCM-25 | Dermic Irritation of the Product on Rabbits—Multiple 3-day Dose. | At up to five times greater than the proposed human dosing over three 24-hour applications, there was no irritability on the test rabbit. |
| D | ION GEL ZCM-25 | Dermic Irritation of the Product on Rabbits—Single Dose. | On a topical administration over one day at the proposed human dosing there was no irritability or adverse reactions on the test rabbits |
| E | ION GEL ZCM-25 | Dermic Irritation of the Product on Humans. Chronic dosing over 14 Days with 20 trial subjects. Completed as a fully registered Clinical Phase 1 Trial | No irritability or adverse reactions on the 20 clinical trial subjects following 14 days of administration at the proposed human dosing. |

While the above description contains much specificity, these should not be construed as limitations on the scope of any embodiment, but as exemplifications of the presented embodiments thereof. Many other alternative embodiments and variations are possible within the teachings of the various embodiments. While the invention has been described with reference to exemplary embodiments, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention will not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are, unless otherwise stated, used in a generic and descriptive sense only and not for purposes of limitation, the scope of the invention therefore not being so limited. Moreover, the use of the terms first, second, etc. do not denote any order or hierarchy of importance, but rather the terms first, second, etc. are used to distinguish one element from another. Furthermore, the use of the terms a, an, etc. do not denote a limitation of quantity, but rather denote the presence of at least one of the referenced items.

While the invention has been described, exemplified, and illustrated in reference to certain preferred embodiments thereof, those skilled in the art will appreciate that various changes, modifications, and substitutions can be made therein without departing from the spirit and scope of the invention.

It is intended, therefore that the invention be limited only by the scope of the claims which follow, and that such claims be interpreted as broadly as is reasonable.

What is claimed is:

1. An aqueous solution comprising:

(i) ammonium ion [$NH_4^+$] in a concentration of 0.01% to 0.64% w/w;

Sulfuric Acid [$H_2SO_4$] in a concentration of less than or equal to 4.5% w/w;

copper ion concentration is to 1% to 3% w/w;

zinc ion concentration is 2% to 8.0% w/w;

wherein the aqueous solution has a pH less than or equal to 1.0; or (ii) a dilution of aqueous solution of (i) wherein the pH is less than 6.

2. The aqueous solution of claim 1, wherein the solution comprises an inert carrier and at least one excipient.

3. The aqueous solution of claim 1, wherein the aqueous solution is diluted before administration.

4. The aqueous solution of claim 1, adjusted to a pH pf about 1.5 to 6.

5. The aqueous solution of claim 1, wherein the solution is configured for administration as a spray or drops; in at least one of a liquid form, a suspension form, or a capsule form.

6. The aqueous solution of claim 1, wherein administration of the solution is configured for cancer treatment.

7. The aqueous solution of claim 1, wherein administration of the solution is configured for inducing an immune response.

8. The aqueous solution of claim 1, wherein administration of the solution is configured for reducing inflammation.

9. The aqueous solution of claim 1, wherein administration of the solution is configured for rejuvenating mitochondrial function.

10. The aqueous solution of claim 1, wherein the solution is configured for dermatological treatment.

11. The aqueous solution of claim 1, wherein administration of the solution is an antimicrobial treatment.

12. The aqueous solution of claim 1, further comprising magnesium ion concentration is less than or equal to 3% w/w.

13. The aqueous solution of claim 1, further comprising a manganese ion concentration of 0.10 to 3% w/w.

14. The aqueous solution of claim 1, further comprising selenous acid concentration of about 0.10% to about 2.0% w/w.

15. The aqueous solution of claim 1, further comprising at least one essential element necessary for normal mammalian biological function.

16. The aqueous solution of claim 1, wherein the aqueous solution comprises at least one of the following ionic essential elements: Boron (B), Calcium (Ca), Chloride (Cl), Cobalt (Co), Copper (Cu), Fluoride (F), Iodine (I), Iron (Fe), Magnesium (Mg), Manganese (Mn), Molybdenum (Mo), Nickel (Ni), Phosphorus (P), Potassium (K), Selenium (Se), Sodium (Na), Sulfur (S), Zinc (Zn).

17. A method of treating cancer comprising administering the aqueous solution of claim 1, to a subject having cancer.

18. A method of reducing inflammation comprising administering the aqueous solution of claim 1 to a subject in need thereof.

19. A method of treating a microbial infection comprising administering the aqueous solution of claim 1 to a subject in need of antimicrobial treatment.

* * * * *